US006228647B1

(12) United States Patent
Voytas et al.

(10) Patent No.: US 6,228,647 B1
(45) Date of Patent: May 8, 2001

(54) TRANSPOSABLE ELEMENT PROTEIN THAT DIRECTS DNA INTEGRATION TO SPECIFIC CHROMOSOMAL SITES

(75) Inventors: Daniel F. Voytas; Xiaowu Gai, both of Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/232,446

(22) Filed: Jan. 15, 1999

Related U.S. Application Data
(60) Provisional application No. 60/071,383, filed on Jan. 15, 1998.

(51) Int. Cl.[7] .............................. C12N 15/85; C07H 21/04
(52) U.S. Cl. ........................................... 435/455; 536/23.1
(58) Field of Search ............................. 435/455; 536/23.1

(56) References Cited

U.S. PATENT DOCUMENTS

| 5,283,173 | 2/1994 | Fields et al. ............................ 435/6 |
| 5,851,529 | * 12/1998 | Guber et al. ...................... 424/188.1 |

OTHER PUBLICATIONS

<http://www.ncbi.nlm.hih.gov:80/entrez/>, accession No. AAC02631, 1994.*
Atwood et al. (1966) "The Retrotransposon Tf1 Assembles Virus–Like Particles That Contain Excess Gag Relative to Integrase Because of a Regulated Degradation Process" *Molecular and Cellular Biology* 16:338–346.
Bell et al. (1993) "Yeast Origin Recognition Complex Functions in Transcription Silencing and DNA Replication" *Science* 262:1844–1849.
Biessmann, et al. (1990) "Addition of Telomere–Associated HeT DNA Sequences 'Heals' Broken Chromosome Ends in Drosophila" *Cell* 61:663–673.
Boeke et al. (1988) "A General Method for the Chromosomal Amplification of Genes in Yeast" *Science* 239:280–282.
Boeke and Sandmeyer (1991) "Yeast Transposable Elements" *The Molecular and Cellular Biology of the Yeast Saccharomyces* Cold Spring Harbor Laboratory Press, Cold Spring Harbor, New York, pp. 193–261.
Brand et al. (1985) "Characterization of a 'Silencer' in Yeast: A DNA Sequence With Properties Opposite to Those of a Transcriptional Enhancer" *Cell* 41:41–48.
Brown et al. (1992) "The Human XIST Gene: Analysis of a 17 kb Inactive X–Specific RNA That Contains Conserved Repeats and Is Highly Localized Within the Nucleus" *Cell* 71:527–542.
Chalker and Sandmeyer (1993) "Sites of RNA Polymerase III Transcription Initiation and Ty3 Integration at the U6 Gene are Positioned by the TATA Box" *Proc. Natl. Acad. Sci. USA* 90:4927–4931.
Chalker and Sandmeyer (1992) "Ty3 Integrates Within the Region of RNA Polymerase III Transcription Initiation" *Genes & Development* 6:117–128.

(List continued on next page.)

*Primary Examiner*—Robert A. Schwartzman
*Assistant Examiner*—Katharine F Davis
(74) *Attorney, Agent, or Firm*—Greenlee, Winner and Sullivan, P.C.

(57) ABSTRACT

The present invention provides methods for altering the integration site specificity of retrotransposons and retroviruses by modifying the integrase protein (especially via engineering its coding sequence) to include a peptide portion which interacts specifically with a protein associated with a chromosome, e.g., a transcription factor, or which interacts with a particular nucleic acid sequence. Further disclosed is a peptide portion of the integrase of Ty5 which peptide portion directs integration of Ty5 or any other retrotransposon or retrovirus into whose integrase it is included into silent chromosome regions and mutant Ty5 integrase proteins for which the insertional specificity is destroyed.

16 Claims, 6 Drawing Sheets

OTHER PUBLICATIONS

Chien et al. (1993) "Targeting of SIR1 Protein Establishes Transcriptional Silencing at HM Loci and Telomeres in Yeast" *Cell* 75:531–541.

Curcio and Morse (1997) "Tying Together Integration and Chromatin" *Trends Genetics* 12:436–438.

Curcio and Garfinkel (1991) "Single–Step Selection for Ty1 Element Retrotransposition" *Proc. Natl. Acad. Sci. USA* 88:936–940.

Devine and Boeke (1996) "Integration of the Yeast Retrotransposon Ty1 Is Targeted To Regions Upstream of Genes Transcribed by RNA Polymerase III" *Genes & Development* 10:620–633.

Diffley and Stillman (1988)"Purification of a Yeast Protein That Binds to Origins of DNA Replication and a Transcriptional Silencer" *Proc. Natl. Acad. Sci. USA* 85:2120–2124.

Dildine et al. (1998) "A Chimeric Ty3/Moloney Murine Leukemia Virus Integrase Protein Is Active In Vivo" *Journal of Virology* 72:4297–4307.

Dujon et al. (1994) "Complete DNA Sequence of Yeast Chromosome XI" *Nature* 369:371–378.

Gai and Voytas (1998) "A Single Amino Acid Change in the Yeast Retrotransposon Ty5 Abolishes Targeting To Silent Chromatin" *Molecular Cell* 1:1015–1055.

Gallay et al. (1997) "HIV–1 Infection of Nondividing Cells Through the Recognition of Integrase by the Importin/Karyopherin Pathway" *Proc. Natl. Acad. Sci. USA* 94:9825–9830.

Ji et al. (1993) "Hotspots for Unselected Ty1 Transposition Events on Yeast Chromosome III Are Near tRNA Genes and LTR Sequences" *Cell* 173:1007–1018.

Kalpana et al. (1994) "Binding and Stimulation of HIV–1 Integrase by a Human Homolog of Yeast Transcription Factor SNF5" *Science* 266:2002–2006.

Karpen and Spradling (1992) "Analysis of Subtelomeric heterochromatin in the Drosophila Minichromosome Dp1187 by Single P Element Insertional Mutagenesis" *Genetics* 132:737–753.

Ke and Voytas (1997) "High Frequency cDNA Recombination of the Saccharomyces Retrotransposon Ty5: The LTR Mediates Formation of Tandem Elements" *Genetics* 147:545–556.

Keeney etr al. (1995) "Multiple Molecular Determinants for Retrotransposition in a Primer tRNA" *Molecular and Cellular Biology* 15:217–226.

Kenna et al. (1998) "Invading the Yeast Nucleus: A Nuclear Localization Signal at the C Terminus of Ty1 Integrase Is Required for Transposition In Vivo." *Molecular and Cellular Biology* 18:1115–1124.

Kikuchi et al. (1995) "Unusual Priming Mechanism of RNA–Directed DNA Synthesis in copia Retrovirus–Like Particles of Drosophila" *Nature* 323:824–826.

Kirchner et al. (1995) "Requirements of RNA Polymerase III Transcription Factors For in Vitro Position–Specific Integration of a Retroviruslike Element" *Science* 267:1488–1491.

Laurenson and Rine (1992) "Silencers, Silencing, and Heritable Transcriptional States", *Microbiological Reviews* 56:543–560.

Levis et al. (1993) "Transposons in Place of Telomeric Repeats at a Drosophila Telomere" *Cell* 75:1083–1093.

Loo and Rine (1994) "Silencers and Domains of Generalized Repression" *Science* 264:1768–1771.

Moore et al. (1998) "A Ty1 Integrase Nuclear Localization Signal Required For Retrotransposition" *Molecular and Cellular Biology* 18:1105–1114.

Moore and Garfinkel (1994) "Expression and Partial Purification of Enzymatically Active Recombinant Ty1 Integrase in *Saccharomyces cerevisiae*" *Proc. Natl. Acad. Sci. USA* 91:1843–1847.

Oliver et al. (1992) "The Complete DNA Sequence of Yeast Chromosome III" *Nature* 357:38–46.

Palladino et al. (1993) "SIR3 and SIR4 Proteins Are Required For the Positioning and Integrity of Yeast Telomeres" *Cell* 75:543–555.

Pimpinelli et al. (1995) "Transposable Elements Are Stable Structural Components of *Drosophila melanogaster* heterochromatin" *Proc. Natl. Acad. Sci. USA*. 92:3804–3808.

Roth, S. (1995) "Chromatin–Mediated Transcriptional Repression in Yeast" *Current Opinion in Genetics and Development* 5:168–173.

Sandmeyer et al. (1990) "Integration Specificity of Retrotransposons and Retroviruses" *Annu. Rev. Genet.* 24:491–518.

SanMiguel et al. (1996) "Nested Retrotransposons in the Intergenic Regions of the Maize Genome" *Science* 274:765–768.

Thompson et al. (1994) "Clustal W: Improving the Sensitivity of Progressive Multiple Sequence Alignment Through Sequence Weighting, Position–Specific Gap Penalties and Weight Matrix Choice" *Nucleic Acids Research* 22:4673–4680.

Varmus and Brown "Retroviruses" In *Mobile DNA* (ed. D.E. Berg and M.M. Howe) American Society for Microbiology, Washington, D.C. pp. 53–108.

Voytas and Ausubel (1988) "A Copia–Like Transposable Element Family in *Arbidopsis thaliana*" *Nature* 336:242–244.

Voytas and Boeke (1992) "Yeast Retrotransposon Revealed" *Nature* 358:717.

Voytas and Boeke (1993) "Yeast Retrotransposons and tRNAs" *Trends in Genetics* 9:421–417.

Xiong and Eickbush (1990) "Origin and Evolution of Retroelements Based Upon Their Reverse Transcriptase Sequences" *The EMBO Journal* 9:3353–3362.

Zou and Voutas (1997) "Silent Chromatin Determines Target Preference of the Saccaromyces Retrotransposon Ty5" *Proc. Natl. Acad. Sci. USA* 94:7412–7416.

Zou et al. (1996a) "The Saccharomyces Retrotransposon Ty5 Integrates Preferentially Into Regions of Silent Chromatin at the Telomeres and Mating Loci" *Genes & Development* 10:634–645.

Zou et al. (1996b) "The Saccharomyces Retrotransposon Ty5 Influences the Organization of Chromosome Ends" *Nucleic Acids Research* 24:4825–4831.

Zou et al. (1995) "The Saccharomyces Ty5 retrotransposon Family is Associated With Origins of DNA Replication at the Telomeres and the Silent Mating Locus HMR" *Proc. Natl. Acad. Sci. USA*. 92:920–924.

* cited by examiner

WT                               M3

HIV
RT | Zn | D,D E | |

MoMLV
RT | Zn | |

Gypsy
RT | Zn | |

Copia
| Zn | | RT |

Tnt1
| Zn | | RT |

Ty1
| Zn | | RT |

Ty5
| Zn | | RT |

```
Ty1  TTINSKKRSLEDNETEIKVSRDTWNTKNMRSLE..PPRSKK.RIHLIAAVKAVKSIKPIR
Ty2  TTTKSKKRSLEDNETEIEVSRDTWNNKNMRSLE..PPRSKK.RINLIAAIKGVKSIKPVR
Ty4  AFLNKEFSSL..NMKRKRKRHDKNNSLTSYELERDKKRSKKNRVKLIPDNMETVSAPKIR
Ty5  DVGDTDLTPA...VTRLVTEENSIESPPSLDSS..PPNTSF.NAALTAIIHSTK..KGNP
                                                        ┌ RT
Ty1  TTLRYDEAITYNKDIKEKEKYIEAYHKEVNQLLKMKTWDTDEYYDRKEIDPKRVINSMFI
Ty2  TTLRYDEAITYNKDNKEKDRYVEAYHKEISQLLKMNTWDTNKYYDRNDIDPKKVINSMFI
Ty4  AIY.YNEAISKNPDLKEKHEYKQAYHKELQNLKDMKVFDVDVKYSRSEIPDNLIVPTNTI
Ty5  KTY..AQAMGR.PDFQEWH...NACLKELSAFKDHNTYKLVSLPKQ.....RRALGSRWV

Ty1  FNKKRDGTHKARFVARGDIQHPDTYDSGMQSNTVHHYALMTSLSLALDNNYYITQLDISS
Ty2  FNKKRDGTHKARFVARGDIQHPDTYDSDMQSNTVHHYALMTSLSIALDNDYYITQLDISS
Ty4  FTKKRNGIYKARIVCRGDTQSPDTY.SVITTESLNHNHIKIFLMIANNRNMFMKTLDINH
Ty5  FTIKDSGTYKARLVAQGHTQKAGIDYQETFAPVIRYDSVRLFLALASCLKLIVYQMDVDT
```

FIG. 2B

TRANSPOSABLE ELEMENT PROTEIN THAT DIRECTS DNA INTEGRATION TO SPECIFIC CHROMOSOMAL SITES

CROSS REFERENCE TO RELATED APPLICATION

This application claims priority from U.S. Provisional application Ser. No. 60/071,383, filed Jan. 15, 1998, which application is incorporated by reference herein to the extent that it is not inconsistent with the present Specification.

BACKGROUND OF THE INVENTION

The field of this invention is molecular biology, particularly in the area of retrotransposons, nucleotide sequence encoding integrase therefrom, and molecular genetic methods based thereon. In particular, the present invention relates to the insertion of heterologous DNA into eukaryotic genomes at specific locations and to protein domains targeting insertion at particular genomic sites.

Retroelements, which include the retroviruses and retrotransposons, insert cDNA copies of themselves into the host genome as part of their replication cycle. The selection of integration sites is not random. While a target bias for the retroviruses is not apparent from the genomic distribution of insertions, they often show local target preferences and tend to integrate into transcriptionally active or DNase I hypersensitive regions [Sandmeyer et al. (1990)]. This suggests that integration sites are not determined by a preference for specific DNA sequences. Rather, target choice is likely mediated by higher order structural features of the target sites (e.g. chromatin) [Curcio and Morse (1997)].

Target biases are clearer for the retrotransposons, particularly those of *Saccharomyces cerevisiae*. The Ty3 elements preferentially integrate upstream of genes transcribed by RNA polymerase III (pol III), usually within 1–2 bases of transcription start sites [Chalker and Sandmeyer (1993); Chalker and Sandmeyer (1992)]. The use of in vitro Ty3 transposition assays has shown that loading of transcription factors TFIIIB and TFIIIC onto tRNA gene promoters is sufficient for targeting [Kirchner et al. (1995)]. Ty1 elements typically integrate within a one kb window upstream of genes transcribed by pol III, and pol III transcription is required for Ty1 target choice [Devine and Boeke (1996)]. The data for both Ty1 and Ty3, therefore, indicate that targeting occurs as a consequence of interactions between a component of the retrotransposon integration complex and a host factor localized to sites of pol III transcription. HIV integrase has been found to interact by two-hybrid assays with a transcription factor homolog called ini1 [Kalpana et al. (1994)], implying that selection of target sites through interactions with chromosomal proteins may be a general feature of retroelements. Ini1, however, is not known to target HIV integration.

The yeast Ty5 retrotransposons integrate almost exclusively into telomeric regions and near the silent mating loci HMR and HML [Zou et al. (1996a); Zou et al. (1995)]. These regions are bound in unique chromatin, called silent chromatin, which represses the expression of adjacent genes and plays a role in telomere maintenance [Laurenson and Rine (1992)]. A large number of factors make up silent chromatin, including proteins involved in DNA replication (ORC), transcription factors (RAP1, ABF1) and silent information regulatory proteins (SIR2–SIR4). Mutations in cis-acting sequences that disrupt the assembly of silent chromatin at HMR also abolish Ty5 integration to this locus [Zou and Voytas (1997)]. This indicates that silent chromatin directs Ty5 target choice.

Despite the evidence that retroelements select target sites through interactions with chromosome-localized proteins, neither retroelement nor specific host factors required for targeted integration have been identified heretofore. In contrast to Ty1 and Ty3, for which there are multiple genomic targets (e.g. 274 tRNA genes; http://genome-www.stanford.edu/Saccharomyces), the number of known Ty5 targets are limited to the 32 telomeres and the two silent mating loci. To identify Ty5-encoded proteins required for targeting, we took advantage of this limited number of targets to devise an assay that monitors the frequency of integration to a single plasmid-borne locus. This assay was used to screen for Ty5 mutations that disrupt targeting, and as a consequence, a region near the C-terminus of integrase was identified as the determinant of target choice.

SUMMARY OF THE INVENTION

It is an object of the present invention to provide a retrotransposon protein, termed an integrase herein, which determines the site specificity (or lack thereof) for insertion of the retrotransposon into the genomic DNA of a eukaryotic cell. Specifically, the present invention provides the protein from Ty5 which determines the specificity of that retrotransposon for silent DNA including, but not limited to, telomeres and the yeast silent mating type loci HMR and HML. The coding sequence of this insertion-specificity determining protein, i.e., the integrase is given in Table 3 (SEQ ID NO:1, nucleotides 2852–4827), and the deduced amino acid sequence is given in Table 3 (SEQ ID NO:2). The specificity determining domain of the integrase protein is located from about amino acid residue 1070 to about 1110, or as more narrowly defined, from about amino acid residues 1074 to about 1105, or as further more narrowly defined, from amino acids 1092 to 1097, as given in Table 3 (SEQ ID NO:2).

The present invention further provides a specificity-determining domain of the Ty5 integrase; this domain is from about amino acid 1070 to about 1110 as given in SEQ ID NO:2 (Table 3). Modifications to the amino acid sequence of this domain results in altered insertion site specificity. As specifically exemplified, a replacement of the serine residue at position 1094 of SEQ ID NO:2 results in a loss of insertion site specificity; i.e., insertion into genomic DNA by this mutated Ty5 derivative is substantially random. Identification of this insertion specificity-determining domain (or peptide portion) allows its substitution for the corresponding domain of the integration protein of other retrotransposons or of retroviruses or for other peptides that interact with components of chromatin, including DNA or DNA-associated proteins such that retrotransposon or retrovirus derivatives can be constructed by one of ordinary skill in the art of molecular biology to generate retrotransposon or retroviruses with variations from the normal insertion site specificity (or lack thereof).

The present invention provides a method for target insertion of heterologous (i.e., retroviral or retrotransposon) DNA into silent chromatin. This is accomplished by replacing the wild-type coding region of a portion or by inserting into a wild-type integrase coding sequence a nucleic acid fragment encoding a peptide portion that interacts with chromatin (or a protein bound to chromatin) at a specific location. One example of such a peptide portion is that naturally encoded by Ty5 (determining SEQ ID NO:3). The skilled artisan understands how to select from among synonymous codons according to the prevalent codon usage for the organism in which use of the modified retrotransposon or retrovirus is intended. For example, the Ty4 integrase could be targeted to silent chromatin by replacing the sequence LERD- KKRSKKNR (amino acids 2940 of SEQ ID NO:6) with LDSSPP, by mutating the coding sequence for that portion of the protein with the portion of Ty5 encoding SEQ ID NO:3. Similarly, the sequence encoding LEPPRSKKR (amino acids 32 to 40 in SEQ ID NO:5) can be replaced with the nucleotide sequence encoding SEQ ID NO:3 to give a silent chromatin-specific derivative of Ty2 or Ty1.

The present invention further provides a peptide determining the interaction of one protein with another (target) protein (which in turn interacts with a specific region of DNA) can be substituted for SEQ ID NO:3 within the Ty5 integrase to re-direct the integration of the modified Ty5p element to the region of the genome to which the target protein is bound. The substitution is achieved by oligonucleotide site-directed mutagenesis, for example, of the integrase coding sequence to replace the Ty5 targeting domain coding sequence (for amino acids 1092 to 1097 of SEQ ID NO:2, i.e., nucleotides 4714 to 4731 of SEQ ID NO:1.

In addition, any retrovirus or retrotransposon can be modified to alter integration site specificity. This can be accomplished by modifying the coding sequence of the integrase to insert a sequence encoding a peptide portion that interacts with chromatin. For example, HIV integrase, MoML integrase, Gypsy integrase or Ty3 integrase can be modified by adding the SEQ ID NO:3 coding sequence to the 3' end of the relevant coding sequence (in-frame and before the translation termination codon) by oligonucleotide site-directed mutagenesis or polymerase chain reaction mutagenesis techniques. Modification to add the Ty5-derived silent chromatin targeting sequence directs integration of the modified element to silent chromatin. Other sequences operably inserted which direct specific interactions with a particular chromosome-associated protein or with a specific nucleotide sequence direct site-specific integration of the modified retrotransposon or retrovirus can be substituted for the Ty5-derived sequence.

Also provided by the present invention is a Ty5 derivative which inserts at random locations in the genomic DNA of a target eukaryotic cell into which it is introduced. This Ty5 derivative, termed Ty5M3 herein, is substantially identical to the Ty5 whose nucleotide sequence is given in SEQ ID NO:1. However, in the integrase protein of this derivative, amino acid residue number is 1094 Leu rather than Ser. The mutation in the nucleotide sequence is in the codon at nucleotide numbers 4720–4722 in SEQ ID NO:1. Similarly, the double mutant (amino acid residue 1016 Ser to Asn substitution together with the amino acid residue 1094 Ser to Leu substitution) has the same phenotype (relatively random insertion sites) as the 1094 Ser to Leu substitution only.

Additional mutant Ty5 derivatives which insert more randomly into a chromosome, desirably a yeast cell chromosome, than Ty5 as shown in SEQ ID NO:1 include Ty5M3, Ty5M15, Ty5M31, Ty5M38, Ty5M41, Ty5M46 and Ty5M39 (see Table 3, rut-3, rut-I5, rut-31, rut-38, rut-41, rut-46 and pWW39 entries for the amino acid sequences at the peptide portions of integrase determining integration site specificity) or, in the case of these Ty5 mutant derivatives, the relative lack of integration site specificity.

BRIEF DESCRIPTION OF THE DRAWINGS

FIG. 1A is a diagram and scheme of the plasmid targeting assay (see also the Examples hereinbelow). In step 1, yeast cell patches are grown on synthetic complete glucose media without uracil and leucine (SC-U-L/glu) to select for both donor and target plasmids. Transposition is induced by replica plating patches to SC-U-L/galactose media. Ty5 transposes into either the chromosome or the target plasmid. In step 2, cell patches are replicated to SC-H/glucose medium. Because replication by reverse transcription generates a functional HIS3 gene, this selects for cells with transposition events. For a cell with Ty5 inserted in the target plasmid, selection for the HIS 3 marker retains the target plasmid, and the cell grows into a white colony. A cell with a chromosomal Ty5 insertion, however, grows into a red or red/white sectored colony due to loss of the target plasmid with its ADE2 marker gene A red colony is shown as black in FIG. 1A.

FIG. 1B shows the color phenotype of His$^+$ colonies generated by wild-type and the M3 Ty5 elements. The red/white colonies are indicated as black/white in FIG. 1B.

FIG. 2 illustrates the mutation that abolishes targeted transposition lies at the border of Ty5 integrase and reverse transcriptase.

FIG. 2A shows the organization of pol in retroelements. The integrases of several retroelements are aligned by the conserved D, D -35 E motif of their catalytic core domain, which carries out strand scission and rejoining [Katz and Skalka (1994)]. Zn marks the integrase Zinc finger domain, which is likely involved in DNA binding; RT indicates reverse transcriptase. HIV (human immunodeficiency virus) and MoMLV (Moloney murine leukemia virus) are retroviruses, and the vertical lines marks the boundary between reverse transcriptase and integrase. Gypsy (from *D. melanogaster*) and Ty3 are Ty3-gypsy retrotransposons, and the Ty1-copia group retrotransposons include copia (from *D. melanogaster*), Tnt1) from tobacco), and Ty1 and Ty5. For the Ty1-copia group elements, the vertical line before RT marks the first of seven sequence motifs characteristic of all reverse transcriptases [Xiong and Eickbush (1990)]. The arrow indicates the site of protease cleavage in Ty1.

FIG. 2B shows the amino acid sequence features of the integrase-reverse transcriptase boundary for Ty1 and Ty5. Alignments of amino acid sequences of integrase and reverse transcriptase were carried out for the four *S. cerevisiae* Ty1-copia retrotransposons (Ty 1, Ty2, Ty4, Ty5) using Clustal.W.1.7 [Thompson et al. (1994)]. The Ty1 protease cleavage site is marked by the arrow [Moore and Garfinkel (1994)], and amino acids conserved in at least three of the four elements are depicted by shaded boxes. The beginning of the first conserved amino acid sequence domain of reverse transcriptase is marked [Xiong and Eickbush (1990)]. Lines above Ty1 amino acid residues indicate sequences important for nuclear localization [Kenna et al. (1997); Moore et al. (1997)]. The Ser1094 mutation is boxed. The amino acid sequences of at least a portion of the integrase proteins of Ty1, Ty2, Ty4 and Ty5 are given in SEQ ID NOS:4, 5, 6 and 2 (amino acids 1066 to 1226).

FIGS. 4A shows that the Ty5 targeting domain establishes transcriptional silencing. Silencing occurs regardless of whether the targeting domain is encoded as part of an ~200 amino acid integrase domain (pXW140) or as merely a short, nine amino acid stretch (pXW205).

FIG. 4B shows that targeting domains with a Ser to Leu change at position 1094 no longer effectively establish transcriptional silencing (pXW205, pXW213), as measured by Northern hybridization analysis.

FIG. 5 shows silencing by the Ty5 targeting domain is measured by loss of URA3 expression and failure of cells to grow on SC-Trp-Ura media. The Ser1094 mutation does not establish silencing (pXW215). FIG. 5 shows that URA3 converts 5-FOA to a toxic substance, and silencing by the Ty5 targeting domain is measured by resistance to 5-FOA.

DETAILED DESCRIPTION OF THE INVENTION

A vector is a genetic unit (or replicon) to which or into which other DNA segments can be incorporated to effect replication, and optionally, expression of the attached segment. Examples include plasmids, cosmids, viruses, chromosomes and minichromosomes.

A coding sequence is a nucleotide sequence that is transcribed into MRNA and translated into protein, in vivo or in vitro. The coding sequence of the retrotransposon polyprotein which includes the reverse transcriptase and the integrase which determines specificity for the insertion of the retrotransposon DNA into a target eukaryotic genome is given in SEQ ID NO:1, nucleotides 1441–6321. The deduced amino acid sequence of the polyprotein is given in SEQ ID NO:2. In SEQ ID NO:1, the integrase encoding portion of the Ty5 sequence is from nucleotide 2852 to 4827.

Regulatory sequences are nucleotide sequences which control transcription and/or translation of the coding sequences which they flank.

As used herein, a recombinant DNA molecule is one which is the result of joining of DNA derived from heterologous sources, either by in vitro by molecular biological techniques or selected from man after introducing two or more different DNA molecules into a cell and selecting and/or identifying and isolating a desired result after recombination within that cell. In any case, the present use of the term recombinant DNA molecule requires the hand of man in that heterologous DNAs are combined into a given molecule in vitro or in vivo in a cell into which those heterologous DNA molecules were introduced through human intervention; i.e., the recombinant DNA molecules of the present invention are not molecules which do or which would have occurred in nature.

The nucleotide sequence of Ty5 is provided in Table 4 (SEQ ID NO:1). This transposon is described in Zou et al. (1996a) and in U.S. patent application Ser. No. 08/771,602, filed Dec. 20, 1997, which application is incorporated by reference in its entirety herein to the extent that it is not inconsistent with the present disclosure.

The Ty5 integrase is responsible for the target specificity of Ty5, which inserts preferentially at silent DNA including, but not limited to, telomeric regions of the genome and the yeast silent mating type loci HMR and HML. The Ty5 integrase targeting (specificity determining) domain interacts with proteins bound to the target region of the genomic DNA and thus, directs integration of the retrotransposon at those sites where the integration takes place. The Ty5 integrase is encoded by a polyprotein coding sequence of Ty5 (nucleotides 1441–6321 in SEQ ID NO:1). Proteolytic cleavage results in the release of an integrase protein and a reverse transcriptase protein. The Ty5 integrase integration specificity determining domain is located from about amino acid 1070 to about amino acid 1110, from about amino acid 1074 to about 1105, and as established herein from amino acid 1092 through 1097, with reference to SEQ ID NO:2.

Figure 1A:
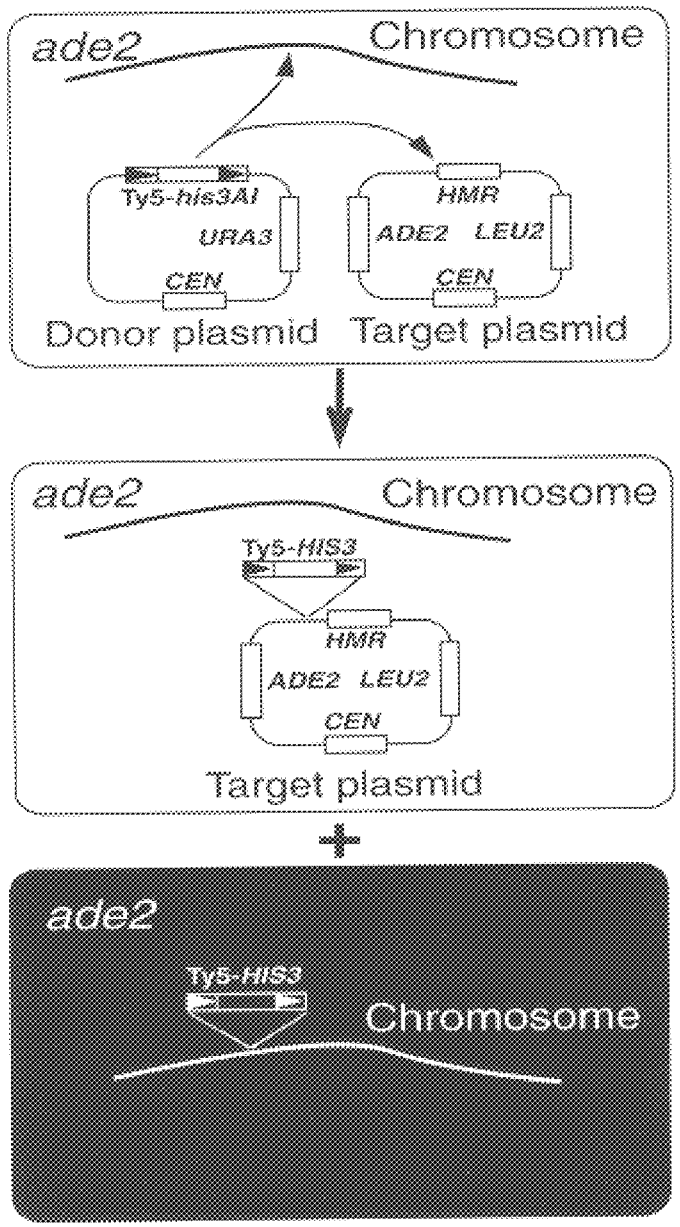
FIGS. 1A–1B illustrate the assay used to monitor transposition to plasmid targets.

The Ty5 targeting assay uses a yeast strain with a plasmid carrying a his3AI-marked Ty5 element under GAL1-10 transcriptional controls (donor plasmid) (FIG. 1A) [Zou et al. (1996a)]. Transposition can be induced by growth on galactose, and replication by reverse transcription of an MRNA intermediate generates a Ty5 element with functional HIS3 gene due to loss of an inactivating intron (AI). Cells containing transposition events, therefore, can be selected by their His+ phenotype. To monitor targeted integration, the yeast strain carries a second plasmid (target plasmid) with a copy of HMR and an ADE2 marker gene. HMR serves as an effective Ty5 target, because its flanking silencers assemble the protein complex recognized by Ty5 [Zou and Voytas (1997)]. The targeting assay was designed such that plasmid integration events give rise to white His+ colonies, and chromosomal integration events give rise to red or red/white sectored His+ colonies.

Figure 1B:
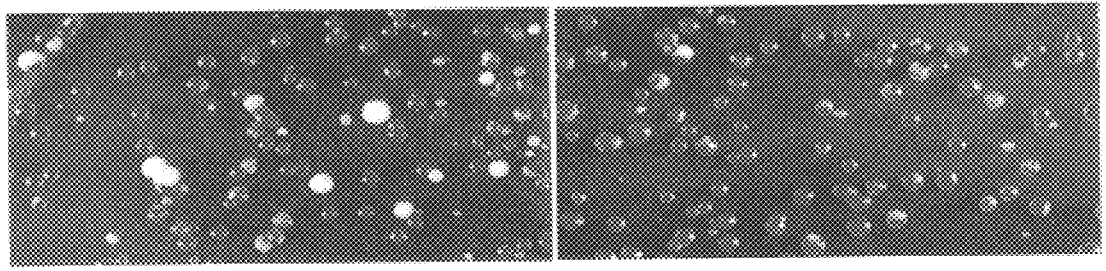

The color phenotype that allows discrimination between plasmid and chromosomal integration events is based on the presence or absence of the target plasmid and its ADE2 marker gene. The parental yeast strain has an ADE2 mutation and is red due to the accumulation of precursors in adenine biosynthesis; sins carrying the target plasmid and the wild type ADE2 gene are white. After induction of transposition, yeast cells are replica plated to media lacking histidine to select for newly transposed Ty5 elements. This media, however, does not select for markers on the original target plasmid. His⁺ cells with insertions on the target plasmid retain this plasmid with its ADE2 marker and therefore grow into white colonies. However, His⁺ cells with Ty5 inserted into the genome lose the target plasmid rapidly, due to lack of selection and plasmid instability caused by CEN/HMR antagonism [Kimmerly and Rine (1987)]. These cells form red colonies or red/white sectored colonies. The preference for Ty5 to integrate into the target plasmid can be simply measured as the ratio of white to total His⁺ colonies. A change in this ratio reflects an altered target specificity (FIG. 1B). We have confirmed that target plasmids from white colonies carry integrated Ty5 elements, and that they have flanking target site duplications indicative of transposition.

Using the targeting assay, we screened a total of 3000 randomly mutagenized donor plasmids for Ty5 elements with altered target specificity. One mutant, M3, showed a greater than 20-fold decrease in the percentage of white colonies, indicating a 20-fold decrease in integration to the target plasmid (FIG. 1B, see also Table 2). To determine whether changes in plasmid targeting reflect changes in chromosomal integration patterns, we recovered ten chromosomal insertions. Sequences at the sites of integration were determined and mapped onto the genome sequence (http://genome-www.stanford.edu/Saccharomyces). We have previously shown that of nineteen independent chr III insertions generated by wild type Ty5 elements, eighteen were clustered at the left telomere or near the E and I transcriptional silencers that flank HMR and HML [Zou et al. (1996a)]. All were within 1.5 kb of our targeting guidepost, the autonomously replicating consensus sequence (ACS) within the silencers or the subtelomeric X repeats. Analysis of 15 wild type Ty5 insertions on other chromosomes revealed that 14 were telomeric, and 12 of these 14 were within 1.5 kb of the X repeat ACS [Zou et al. (1996b)]. In striking contrast, none of the ten integration events generated by M3 were near preferred Ty5 targets (Table 1). Distance to the nearest X repeat ranged from 19 to 599 kb. Half of these insertions were within known genes or hypothetical coding regions. Only five of 34 previously characterized insertions were in open reading frames [Zou et al. (1996a); Zou et al. (1996b)].

To identify the mutation responsible for altered target specificity, restriction fragments from M3 and a wild-type Ty5 element were swapped and chimeric elements retested in the targeting assay (Table 2). This analysis localized the mutation to a 2 kb SphI fragment in M3. DNA sequence analysis revealed two base changes within this fragment that result in amino acid substitutions: Ser to Asn and Ser to Leu substitutions at positions 1017 and 1094 in Ty5's single open reading frame. The two mutations were separated by subcloning, and the resultant constructs were confirmed by DNA sequencing and retested in the plasmid targeting assay. The targeting defect was solely due to the Ser to Leu change at position 1094, demonstrating that a single amino acid change can completely disrupt Ty5 target specificity.

Among the conserved cis sequences within the HM silencers and the subtelomeric X repeats is an autonomously replicating consensus sequence (ACS). We have used this ACS as a convenient guidepost to compare sites of Ty5 insertion; the eighteen telomeric or HM-localized insertions on chr III were within 1.5 kb of this ACS. Analysis of 15 wild type Ty5 insertions on other chromosomes revealed that 14 were telomeric, and 12 of these 14 were within 1.5 kb of the X repeat ACS [Zou et al. (1996b)]. In striking contrast, none of the ten integration events generated by M3 were near preferred Ty5 targets (Table 1). Distance to the nearest X repeat ranged from 19 to 599 kb. Half of these insertions were within known genes or hypothetical coding regions. Only five of 34 previously characterized insertions were in open reading frames [Zou et al. (1996a); Zou et al. (1996b)].

No obvious pattern emerged from analysis of the ten M3 insertion sites. In particular, none of the insertions were at preferred target sites for the other yeast retrotransposons, namely within the upstream regions of genes transcribed by RNA polymerase III. Ty5, therefore, appears to integrate randomly when its normal targeting mechanism is disrupted and does not employ a default targeting pathway.

Saturation mutagenesis was used to further define the Ty5 targeting domain. A 758 bp BspEI to PflMI restriction fragment, which included Ser1094, was randomly mutagenized by PCR. Mutagenized fragments were swapped with the corresponding fragment in a wildtype element to generate a Ty5 mutant library. The collection of mutant elements was screened for targeting defects using our plasmid-based assay. Eleven new mutants were identified that were impaired in targeting to varying degrees. DNA sequencing revealed that all mutants carried multiple amino acid changes within the BspEI to PflMI restriction fragment. Interestingly, all had amino acid changes within a six amino acid stretch (amino acids 1092 to 1097, as given in SEQ ID NO:2) that included Ser1094. In total, four amino acid residues were altered within this six amino acid stretch, resulting in eight different amino acid substitutions. One of these was a Ser to Leu change at position 1094, which is identical to the original, independently derived M3 targeting mutation.

Because all 11 targeting mutants had amino acid substitutions in and around Ser1094, we concluded that these substitutions are responsible for the targeting defects. Seven new Ty5 constructs were made by moving the mutations near Ser1094 into a wildtype element. The only mutation in our collection that was not analyzed was the Ser to Leu change at position 1094. Targeting was tested for each construct, and in all cases the Ty5 elements displayed targeting defects (Table 3); these defects were indistinguishable from the original mutants.

In our two screens for targeting mutants, we recovered multiple mutations in four of the six amino acid residues important for targeting. We concluded, therefore, that our screen was exhaustive and that the Ty5 targeting domain is as short as six amino acid residues in length. To test this, we mutagenized additional flanking amino acid residues by PCR-based, site-directed mutagensis. Mutant elements were tested in our plasmid-based assay, and none were found to have targeting defects (Table 3). We concluded, therefore, that the Ty5 targeting domain is six amino acids in length, from amino acids 1092 to 1097, as given in SEQ ID NO:2.

The organization of pol differs among retroelements. Integrase is the final pol-encoded enzyme among the retroviruses and Ty3-gypsy retrotransposons (FIG. 2A). For the Ty1-copia elements (of which Ty5 is an example), integrase precedes reverse transcriptase and is released from pol by protease cleavage. Ty1-copia elements often have a large coding region of largely undefined function between the core domain of integrase and reverse transcriptase. For Ty1, this region is a large C-terminal extension of integrase, as determined by the mapping of Ty1 protease cleavage sites [Moore and Garfinkel (1994)]. Ty1 protease cleaves between two alanine residues near reverse transcriptase. Although this region is not well-conserved among retrotransposons, amino acid sequence alignments reveal several conserved residues shared between Ty1 and Ty5 near the Ty1 integrase C-terminus, including the two adjacent alanine residues (FIG. 2B). The serine mutation in M3 that disrupts targeted integration lies nine amino acids upstream from the two alanine residues; thus it is within a long C-terminal extension of the Ty5 integrase, and this C-terminal region of the Ty5 integrase mediates target specificity.

As shown in Table 2, the Ser1094 mutation in M3 also causes an approximately 4-fold decrease in overall transposition frequency. In addition to integration, retrotransposon cDNA can enter the genome by recombination with homologous sequences [Ke and Voytas (1997); Sharon et al. (1994)]. The Ser1094 mutation also decreases cDNA recombination to a comparable extent; thus, this mutation affects a step common to the integration and recombination pathways. Candidates for such steps include reverse transription or nuclear localization. In support of the latter, the Ser1094 mutation lies within a region that corresponds to the nuclear localization signal of Ty1 integrase [Kenna et al. (1998); Moore et al. (1998)]. The C-terminus of HIV integrase has also been shown to mediate nuclear localization [Gallay et al. (1997)]. Although the sequence of the Ty1 nuclear localization signal is not conserved in Ty5, a link between Ty5 nuclear localization and targeting is intriguing, since regions of silent chromatin are preferentially associated with the nuclear membrane [Palladino et al. (1993)]. Regardless of the cause of the 4-fold transposition defect, it is clear that integration is still efficient in the mutant, and therefore targeting and integration of the Ty5 transposable element DNA are genetically distinct.

To determine the boundary between Ty5 integrase and reverse transcriptase, we characterized the processed form of reverse transcriptase. To aid in these studies, a polyhistidine epitope tag was inserted at the very C-terminus of reverse trancriptase; monoclonal antibodies are commercially available that recognize this epitope, and because it encodes six adjacent histidine residues, the recombinant protein can be purified by nickel-affinity chromatography. Ty5 elements carrying the epitope tag were found to transpose at near wildtype levels, indicating that the epitope did not compromise reverse transcriptase function. Western blot analyses revealed that yeast cells expressing the marked element accumulate a single protein of approximately 55 kD that reacts with the monoclonal antibody. The immunoreactive protein was purified by nickel chromatography, and its N-terminal sequence was found to be heterogeneous. Without wishing to be bound by any particular theory, we believe that protease cleavage occurs within a window of a few to several amino acids. The best fit of the sequence data to the Ty5 amino acid sequence, however, places the cleavage site at a comparable position to the cleavage site in Ty1 (FIG. 2B). The purified reverse transcriptase was further characterized by cleaving it with CNBr and purifying the cleavage products by high performance liquid chromatography. The fragment profile matched that expected for reverse transcriptase. Based on this data, we conclude that the targeting domain lies within about 12 amino acid residues of the integrase C-terminus. The Ty5 integrase not only carries out the cutting and pasting reactions, but it also selects the sites where integration occurs.

Tethering the Ty5 targeting domain to a crippled HMR silencer reestablishes silencing. Ty5 targeting is efficient: 32/34 or 94% of wild type elements integrate near silent chromatin (Table 1). This efficiency could be explained if targeting is required for integration. However, as shown in Table 2, the Ser1094 mutation only causes a 4-fold decrease in overall transposition frequency. If targeting were a requirement for integration, transposition would be predicted to drop approximately 17-fold (reining the 6% non-targeted integration events). This indicates that targeting and integration are genetically separable.

We considered two possible models to explain the efficiency of Ty5 targeting. In the first model, the targeting domain serves to localize the integration complex within a "silent compartment" of the nucleus. The idea that silent chromatin occupies a separate perinuclear compartment is supported by a variety of genetic and cell biological studies [Wakimoto 1998 and references therein]. For example, silent chromatin is preferentially associated with the nuclear membrane [Palladino et al. (1993)], and transcriptional silencing is induced when marker genes are localized to the nuclear periphery [Andrulis et al. (1998)]. In this model, the Ty5 targeting domain would direct the integration complex to an intranuclear silent compartment, and the observed target patterns would result because only chromosomal sequences located within this compartment could serve as integration sites. This model is supported by the observation that Ty5 targeting domain lies within a region corresponding to the nuclear localization signal of Ty1 integrase [Kenna et al. (1997); Moore et al. (1997)]. The C-terminus of HIV integrase has also been shown to mediate nuclear localization [Gallay et al. (1997)].

A second model to explain the efficiency of Ty5 targeting is that Ty5 integrase interacts directly with a protein component of silent chromatin. In this model, the Ty5 integration complex enters the nucleus, and the targeting domain interacts with a specific protein component of silent chromatin. This effectively tethers the integration machinery and allows for the observed target specificity. Of course, these two models are not mutually exclusive. For example, one domain could localize the Ty5 integration complex within a nuclear subcompartment, and then the targeting domain could tether the integration complex to specific DNA-bound proteins. We favored this second model, and we examined whether or not our targeting domain physically interacts with a chromatin component.

We used a set of well-characterized mutations in the HMR-E silencer [Chien et al. (1993)]. HMR-E contains three binding sites for proteins that are important in silencing (designated A, E and B). Deletion of any two of these sites (generating a crippled silencer) completely abolishes transcriptional repression. Chien et al. have shown that silencing can be restored at a crippled silencer by tethering components of silent chromatin to HMR, such as SIR1, SIR3 or SIR4. Tethering is achieved by adding three copies of a GAL4 binding site (UASg) to HMR-E. The SIR proteins are fused to the GAL4 DNA binding domain (GBD) and expressed in the yeast cell. When the GAL4-SIR fusion protein binds to the UASg, silencing is reestablished because the tethered SIR protein recruits other components of silent chromatin through protein-protein interactions. We reasoned that if our Ty5 targeting domain physically interacts with protein components of silent chromatin, then tethering the Ty5 targeting domain to a crippled HMR silencer should reestablish silencing in a manner similar to the tethered SIR proteins.

Figure 3:
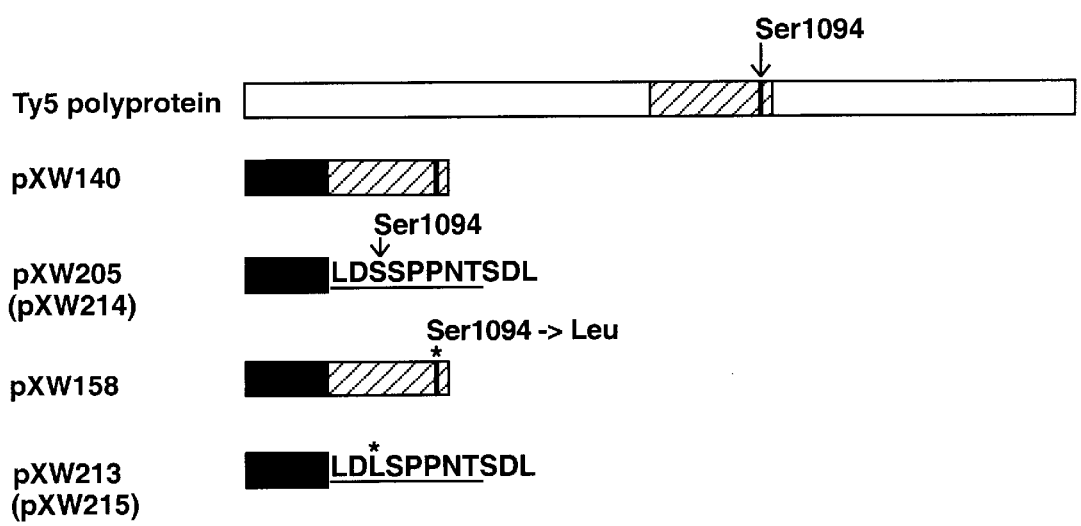
FIG. 3 shows constructs used to demonstrate that the Ty5 targeting domain interacts with components of silent chromatin. The Ty5 polyprotein is shown schematically as a white box. The SphI fragment that encodes most of integrase and part of reverse transcriptase is hatched. Ser1094 is indicated by the arrow. In the remaining constructs, the GAL4 DNA binding domain (GBD) is indicated as black box. The Ser to Leu change at position 1094 is noted by the asterisk. In constructs pXW205 and pXW213, the sequence of 11 amino acids fused to the GBD is shown; the nine Ty5-encoded amino acids are underlined. The Ty1 protease cleavage site is marked by the arrow [Moore and Garfinkel (1994)], and the asterisks mark identical amino acids or conservative substitutions (i.e. D for E, K for R, M, I or L for V). The vertical line marks the beginning of the first conserved amino acid sequence domain of reverse transcriptase [Xiong and Eickbush (1990)], and amino acid residues important for Ty1 nuclear localization are underlined [Kenna et al. (1998); Moore et al. (1998)]. The thick vertical line marks the mutated serine in M3.
Figures 4A, 4B:
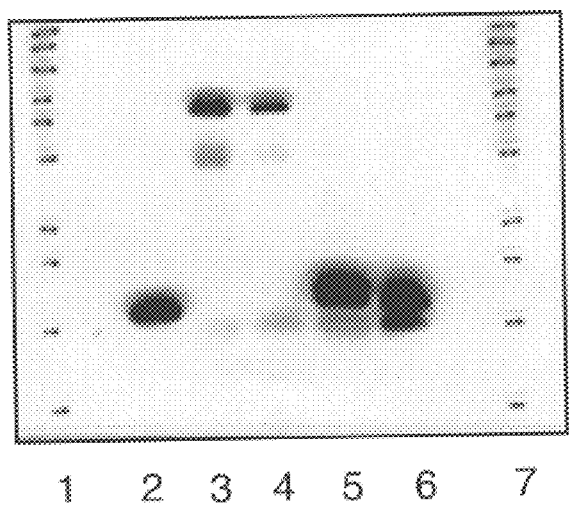
FIGS. 4A–4B show that the Ty5 targeting domain silences a TRP1 marker gene at a crippled HMR-E silencer. Strains YSB1, YSB2 and YSB35 have a TRP1 marker gene at HMR, and so the extent of silencing mediated by HMR-E is measured by growth on SC-Ura-Trp media. Growth on SC-Ura serves as a control for cell number. The genotype of HMR-E is noted by the AEB designation., where small letters indicate mutations at a particular site. UASg indicates GAL4 upstream activation sequences that are bound by the GAL4 DNA binding domain. All constructs are described in FIG. 3.

To test this, we made two constructs, designated pXW140 and pXW205 (FIG. 3). pXW140 expresses a fusion protein between GBD and 256 amino acids of the Ty5 polyprotein in the region encompassing Ser1094. pXW205 expresses a GBD fusion with nine Ty5 amino acid residues at its carboxyl terminus, including the six amino acid residues that comprise the targeting domain. These plasmids were introduced into three strains with crippled silencers: YSB 1 (aeB; the small letters indicate the mutant protein binding sites), YSB2 (aeB) and YSB35 (Aeb). YSB2 and YSB35 carried three UASg sites within HMR-E. To monitor the transcriptional status of the locus, HMR was replaced with a TRP1 marker gene in all three strains; the extent of silencing can be measured by growth on media lacking tryptophan. We found that both GBD fusion proteins could establish silencing in YSB2 and YSB35 but not in the control strain YSB1 (FIG. 4A). Although the larger fusion protein encoded by pXW140 could establish silencing to a greater extent, the nine amino acids encompassing the targeting domain were sufficient for silencing. This remarkable result has two implications: 1) it supports the mutagenesis data which indicated that the targeting domain was limited to a few amino acids; 2) it indicates that the targeting domain interacts physically with protein components of silent chromatin. As a consequence, we can rule out the model wherein the targeting domain primarily serves as a signal for subnuclear localization.

If the targeting domain interacts with components of silent chromatin, mutations that affect targeting would also affect their ability to establish transcriptional silencing. To confirm this, we generated two additional constructs equivalent to those tested above, except that they carry the Ser1094 mutation (FIG. 3): pXW158 is the mutant version of pXW140, and pXW213 is the mutant version of pXW205. We found that in contrast to the wildtype fusion proteins, these constructs failed to establish silencing as they conferred growth on media lacking tryptophan to the same extent as the negative control (a strain expressing the GBD alone; pGBD-UC1) (FIG. 4B). The failure to establish silencing was not due to instability of the mutant fusion proteins. They were expressed to levels comparable to the wildtype proteins (FIG. 4C). These experiments indicate that a single amino acid change within the targeting domain can abolish the physical interaction with silent chromatin components.

Figure 5:
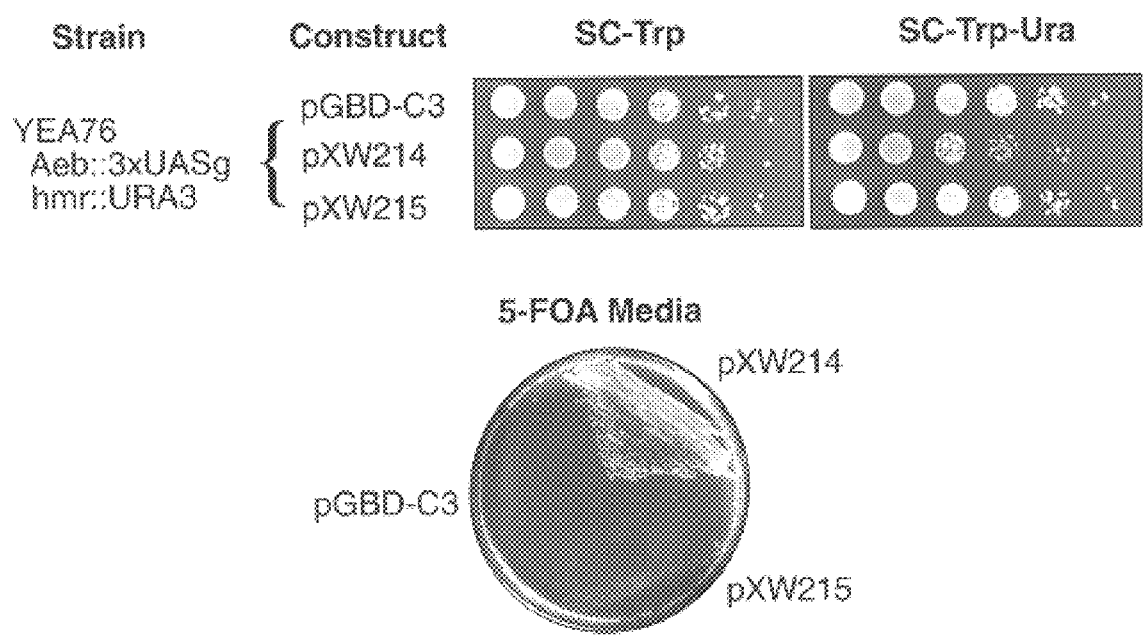
FIG. 5 shows that the Ty5 targeting domain silences a URA3 marker gene at a crippled HMR-E silencer. Strain YEA76 has a URA3 gene at HMR (see FIGS. 3 and 4 for more complete description of strains and constructs).

The fusion proteins encoded by pXW205 and pXW213 were cloned into a TRP 1-based plasmid generating pXW214 and pXW215, respectively. This was done so that the constructs could be used in a second strain (YEA76) that has a URA3 marker integrated at HMR. Silencing in this strain can be measured by two means: loss of URA3 expression prevents cells from growing on media lacking uracil, and lack of URA3 expression confers resistance to 5-fluoroorotic acid (5-FOA) [Boeke et al. (1987)]. Indeed, by both these measures, the fusion protein encoded by pXW205 effectively established silencing and the fusion protein with the Ser1094 mutation did not (FIG. 5). Thus, we conclude that the Ty5 targeting domain is a powerful nucleation site for silent chromatin assembly.

Figure 6:
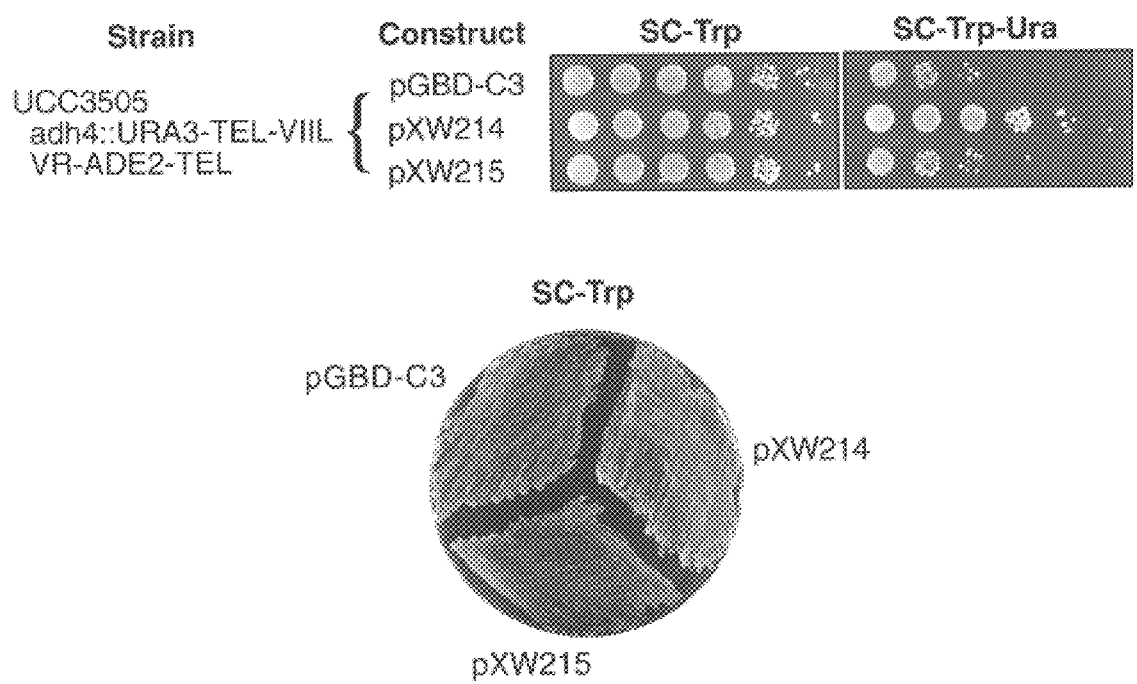
FIG. 6 demonstrates that the expression of the Ty5 targeting domain exerts a telomeric position effect. Strain UCC3505 carries telomeric URA3 and ADE2 marker genes. Silencing of these markers is evidence by poor growth on media lacking uracil and red colony color (see control construct pGBD-C3, which expresses the GAL4 DNA binding domain alone). Expression of the Ty5 targeting domain (pXW214) relieves telomeric silencing, and results in increased growth on media lacking uracil and white colonies. The Ser1094 mutation does not affect telomeric position effect.

Overexpression of the Ty5 targeting domain disrupts the telomere position effect. Transcriptional silencing at the telomeres is sensitive to the stoichiometry of components of silent chromatin. Because the Ty5 targeting domain interacts with one or more of these factors, we predicted that its overexpression would titrate away some silencing factors and relieve the transcriptional repression of marker genes integrated at the telomeres. To test this, we used yeast strain UCC3505, which has ADE2 and URA3 marker genes integrated at separate telomeres [Gottschling et al. (1990)]. Plasmids pXW214, pXW215 and a control plasmid that expresses the GBD alone (pGBD-C3) were introduced into UCC3505. All three plasmids have a high-copy, 2-micron origin of replication, and the fusion proteins are expressed from the strong ADH1 promoter. Expression of the fusion with the wildtype targeting domain (pXW214) relieved the telomere position effect (FIG. 6). This was evidenced by the increased growth of yeast cells on media lacking uracil and the white color of the colonies (loss of ADE2 expression causes a pink phenotype due to accumulation of precursors in adenine biosynthesis). In contrast, the mutant Ty5 targeting domain (pXW215) had no effect on expression of the telomeric marker genes and was equivalent to the negative control (pGBD-C3).

Target site biases observed among retroviruses and retrotransposons are thought to be the consequence of interactions between the retroelement integration complex and chromosome-localized proteins. We have identified the first retroelement-encoded domain responsible for targeted integration. Without wishing to be bound by any particular theory, we believe that the Ty5 targeting domain interacts, either directly of indirectly, with a component of silent chromatin. The discovery of a targeting domain enables the manipulation of retroelement target specificity. This is useful in many areas within molecular biology, especially as related to retroviruses, and for improved vectors for gene therapy. Moreover, using the teachings of the present invention, retroelements can be modified to interact with a variety of DNA-bound proteins and used to map chromosomal locations of transcription factors or components of chromatin.

Retroviral vectors are relatively widely used to deliver DNA to human and other animal cells. However, their pattern of integration is large random, and integration is sometime deleterious in that it causes mutations due to the insertion of several kilobases of heterologous DNA into the genome of the cell into which it has been introduced. The effectiveness of therapeutic genes delivered by retrovirus vectors can be compromised due to integration into regions of the genome which are not conducive to gene expression. With the teachings of the present disclosure, taken with what is well known to the art, the integration site specificity of retroviruses and retrotransposons can be altered by engineering the carboxyl terminus of the integrase so that the engineered integrase interacts with target protein components of chromatin. This results in specific integration wherever the target protein is located on the chromosome. In the case of Ty5, targeting is the result of specific interactions between the carboxyl terminus of the Ty5 integrase and a component of silent chromatin. The engineering of an integrase is preferably carried out at the nucleic acid level, with the wild-type coding sequence of the integrase being modified by PCR mutagenesis, oligonucleotide site-directed mutagenesis or endonuclease cutting and ligation to add or substitute a sequence encoding a peptide portion determining the desired interaction or by replacing the wild-type coding region determining integration site specificity with a nucleotide coding sequence determining a peptide portion directing a desired interaction and thus, a desired integration site specificity. With the teachings of the present disclosure, the specificity determining domain of the Ty5 or of an other integrase protein can be engineered as a carboxyl terminus to a retroviral integrase, with the result that the retrovirus adopts the insertion specificity of the retrotransposon integrase from which the domain is derived. For example, addition of the specificity determining domain of Ty5 causes specific insertion into silent DNA, such as a telomeric region in a genome or a yeast silent mating type locus such as HMR or HML. Alternatively, if random insertion is desired the specificity determining domain of the Ty5 derivative Ty5M3 described herein can be expressed as a C-terminal domain of a retroviral or retrotransposon integrase. Alternatively, the domain of a protein which specify the interaction of that protein with a particular second protein which associates with a particular location (i.e. nucleotide sequence) can be engineered to create a Ty5 derivative having that heterologous domain replacing amino acids 1070–1110 of the wild-type Ty5 integrase, with reference to the numbering in Table 3 hereinbelow. The present disclosure enables a new method for gene identification by retrotransposon tagging, where the retrotransposon in to be inserted next to any known DNA-binding protein, including but not limited to a transcription factor which regulates the expression of one or more genes and for which the nucleotide coding sequence of the transcription factor is known or can be readily determined by routine experimentation.

Phage display-combinatorial chemistry technology, well known to the artisans in the field of molecular biology, is applied to the identification of ligand-binding peptide sequences. In the context of the present invention, the "ligand" can be a protein which associates with particular regions of a chromosome, for example, a transcription factor (positive or negative regulator of transcription). Transcription factor-binding regions can be identified using this technology, where binding of a particular displayed peptide sequence to the particular transcription factor is detected. Genetic engineering of an integrase coding sequence to contain a nucleotide sequence encoding this peptide sequence in a retrotransposon or retrovirus results in integration of the modified retrotransposon or retrovirus at or near all chromosomal sites of action for that transcription factor, thereby allowing the identification of genes regulated by that transcription factor. See, e.g., Hoogenboom et al. (1998) *Immunotechnology* 4:1–20, and references cited therein.

An application of the present technology, taking advantage of the silent chromatin targeting of Ty5, is the tagging of genes which are affected by aging in the sense, that during the aging process, these genes become bound by silent chromatin binding proteins, including but not limited to those silent chromatin binding proteins which are bound to telomeres in cells which are not considered to have aged or which are bound to the silent mating type loci HML or HMR of yeast. At least one of these silent chromatin binding proteins interacts with the integration specificity determining domain of the Ty5 integrase protein, with the result that the Ty5 (or derivative thereof) becomes inserted into the genome at a site where the silent chromatin binding protein has bound. By generating a sufficiently large population of Ty5 insertions, one can generate a collection of insertion mutations in which substantially all genes to which a silent chromatin binding protein (such as a telomere binding protein) binds during the aging process. The insertion of the Ty5 at or near these genes allows their cloning due to the identifying Ty5 sequence tag. Genomic DNA can be prepared from this mutant collection, the DNA preparation can be digested with one or more restriction endonucleases of choice, the digestion products can be ligated (cloned) into a vector of choice, and the "tagged" genes can be identified from the collection of clones by sequence hybridization/ homology to a Ty5 probe or by polymerase chain reaction technology using one or more Ty5 primers and one or more appropriate vector primers, as readily understood by one of ordinary skill in the art of molecular biology.

A further application of this technology is in the study of oncogenes. Many oncogenes are transcription activating proteins that bind to chromosomal DNA at particular sites and which regulate the transcription of multiple genes. Using two hybrid screen technology (see, for example, U.S. Pat. No. 5,283,173, incorporated by reference herein in its entirety) one can readily isolate an oncogene-specific integrase specificity determining domain of a Ty5 derivative using the interaction of a Ty5 domain derivative by its positive interaction with at least one oncogene transcription activating protein used as the partner in the two hybrid screen. Then the Ty5 derivative which specifically interacts with the oncogene transcription activator can be used in retrotransposon insertion mutagenesis schemes to tag the genes with which the oncogene transcription activator binds in the genome of a eukaryotic cell of interest.

Methods for the introduction of genetic material into plant cells and tissue are well known to the art. Within the context of marking cells or tissue or a plant, the Ty5 derivative altered to contain a plant-expressible gene is introduced on a DNA vector which on its own cannot integrate or replicate in plant cells. Genetically engineered plant cells or tissue can be identified by a hybridization or polymerase chain reaction. Where an plant-expressible selectable marker is used, standard selection of the genetically engineered plant cells or tissue can be carried our using standard, well known methods. A preferred selectable marker is the kanamycin resistance marker from Ty5. Methods for the genetic manipulation of plant cells and tissue, include but are not limited to *Agrobacterium tumefaciens*-mediated DNA transfer, preferably with a disarmed T-DNA vector, electroporation, direct DNA transfer, and particle bombardment [see Davey et al. (1989) *Plant Mol. Biol.* 13:275; Walden and Schell (1990) *Eur. J Biochem.* 192:563; Joersbo and Burnstedt (1991) *Physiol. Plant.* 81:256; Potrykus (1991) *Annu. Rev. Plant Physiol. Plant Mol. Biol.* 42:205, Gasser and Fraley (1989) *Science* 244:1293; Leemans (1993) *Bio/Technol.* 11:522; Beck et al. (1993) *Bio/Technology* 11:1524; Koziel et al. (1993) *Bio/Technology* 11:194; Vasil et al. (1993) *Bio/Technology* 11:1533]. Techniques are well known to the art for the introduction of DNA into monocots as well as dicots, as are the techniques for culturing such plant tissues and regenerating those tissues. Monocots which have been successfully transformed and regenerated include wheat, corn, rye, rice and asparagus. For efficient regeneration of transgenic plants, it is desired that the plant tissue used in the transformation possess a high capacity to produce shoots. For example, tobacco leaf discs and aspen stem sections have good regeneration capacity [Sitbon, F. (1992) supra].

Techniques for introducing and selecting for the presence of heterologous DNA in plant tissue are well known. For example, *A. tumefaciens*-mediated DNA transfer into plant tissue, followed by selection and growth in vitro and subsequent regeneration of the transformed plant tissue to a plant is well known for a variety of plants.

Other techniques for genetically engineering plant tissue to contain an expression cassette comprising a suitable promoter fused to the coding sequence of interest and containing a transcription termination region are to be integrated into the plant cell genome by electroporation, cocultivation, microinjection, particle bombardment and other techniques known to the art. The expression cassette further contains a marker allowing selection of the expression cassette in the plant cell, e.g., genes carrying resistance to an antibiotic such as kanamycin, hygromycin, gentamicin, or bleomycin. The marker allows for selection of successfully transformed plant cells growing in the medium containing certain antibiotic because they will carry the expression cassette with resistance gene to the antibiotic.

Animal cells and tissue are also amenable to genetic manipulation to contain heterologous DNA according to well known methods, including but not limited to electroporation, particle bombardment, liposomes, receptor-mediated endocytosis, polyethylene glycol mediated transformation and other methods for transfection and transformation [see, e.g., *Methods in Enzymology,* Vol. 217]. Selection techniques and markers, where desired, are also well known to the skilled artisan.

Yeast genetic and molecular biology techniques are described in (e.g.) *Meth. Enzymol.* Vol. 194 [C. Guthrie and G. R. Fink, eds.].

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art A number of standard techniques are described in Sambrook et al. (1989) *Molecular Cloning,* Second Edition, Cold Spring Harbor Laboratory, Plainview, N.Y.; Maenads et al. (1982) *Molecular Cloning,* Cold Spring Harbor Laboratory, Plainview, N.Y.; W (ed.) (1993) *Math. Ensemble.* 218, Part I; W (ed.) (1979) *Math Ensemble.* 68; W et al. (eds.) (1983) *Math Ensemble.* 100 and 101; Grossman and Moldave (eds.) *Math Ensemble.* 65 Miller (ed.) (1972) *Experiments in Molecular Genetics,* Cold Spring Harbor Laboratory, Cold Spring Harbor, N.Y.; Old and Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; and Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein. All references cited in the present application are incorporated by reference in their entirety herein to the extent that there is no inconsistency with the present disclosure.

The foregoing discussion and the following examples are provided for illustrative purposes, and they are not intended to limit the scope of the invention as claimed herein. Modifications and variations which may occur to one of ordinary skill in the art are within the intended scope of this invention.

EXAMPLES

Example 1. Mutagenesis and Screens

The yeast strain used in this study was YNK313 (MATα, GAL4+, trp1Δ63, ura3-52, leu2Δ1, his3Δ200, lys2-801, ade2-101, rad52::trp1), a derivative of YPH499. The target plasmid (pXW78) contains a 3.7 kb BamHI fragment with ADE2 from pJK204 [Keeney et al. (1995)] and a 4.0 kb BamHI-XhoI fragment with the HMR locus from pJA82.6× 268 [Abraham et al. (1984)]; both were cloned into pRS425 [Sikorski and Hieter (1989)]. The donor plasmid (pNK254 [Zou et al. (1996a)]) was mutagenized by growing for two days in the *E. coli* strain XL1-Red (Stratagene), which carries mutations in multiple DNA repair pathways. Mutagenized donor plasmids were transformed into YNK313 with pXW78 and independent transformants were screened for Ty5 targeting defects as described in FIG. 1 (see also below).

Saturation mutagenesis of the BspEI/PflMI fragment encompassing Ser1094 was carried out by PCR-based mutagenesis (Amersham, Inc.). PCR-based site directed mutagenesis was used to make specific amino acid changes within the Ty5 targeting domain [Ausubel et al. (1989)].

Example 2. Transposition Assays

Transposition frequencies were determined as previously described [Zou et al. (1996a)], with the exception that the induction of transposition on galactose media was carried out for 3 days. Targeting was measured by patching yeast cells with the donor and target plasmid onto SC-U-L/glucose plates and growing for 2 days at 30° C. Patches were replica plated to SC-U-L/galactose media and grown for 3 days at 22° C. In screens for Ty5 mutants, cell patches were replica-plated onto SC-H media with 6 mg/l adenine to visualize the relative number of white or red and red/white sectored colonies. To confirm candidate mutants or to quantitate targeting, cells were scraped after growth on galactose, resuspended in water and plated onto SC-H media with limited adenine. Colonies were scored for their color after growth for 4 days at 30° C.

Example 3. Recovery of Chromosomal Insertions

Independent transposition events were generated by the M3 element in strain W303-1A (MATα ade2-1 can1-100 his3-11 leu2-3 trp1-1ura3-1); we have previously used this strain to evaluate wild type Ty5 target preference [Zou et al. (1996a); Zou et al. (1996b)]. Insertion sites were determined either by inverse PCR as previously described or by plasmid rescue. For plasmid rescue, the integration plasmid pSZ274 was linearized with EcoRI and used to transform strains carrying Ty5 insertions; pSZ274 carries a fragment of Ty5 integrase cloned into pRS306 [Sikorski and Hieter (1989)]. Transformants in which plasmid DNAs had recombined with chromosomal insertions were selected using the URA3 marker. Genomic DNAs were prepared, digested with Sa/I and XhoI or SpeI and xbaI, ligated and transformed into *E. coli* to recover plasmids with either 5' or 3' flanking sequences. DNA sequences at the site of M3 insertion were obtained with the universal and reverse primers.

Example 4. Tethering and Overexpression of the Ty5 Targeting Domain

To generate the fusion proteins, mutant and wildtype Ty5 sequences were cloned into pGBD or pGBDU plasmids [James et al. (1996)]; these plasmids contain the GAL4 DNA binding domain expressed under the control of the ADH1 promoter. The resulting plasmids were transformed into the appropriate strains listed in FIG. 4 [Andrulis et al. (1998)]. An overnight culture was grown to saturation for each strain and 10 fold serial dilutions were made; 10 microliter aliquots of each dilution was spotted onto both the test plate and the control plate. The plates were incubated at 30° C.

Example 5. Protein Analyses

Yeast proteins were prepared as described [Ausubel et al. (1987)]. Western analyses were conducted using antibodies specific to the GAL4 DNA binding domain (Clontech, Inc.).

The methods for epitope-tagging and nickel-chromatography purification of reverse transcriptase were supplied by the manufacturer (Qiagen, Inc., Chatsworth, Calif.). Purified reverse transcriptase was separated by SDS polyacrylamide gel electrophoresis, transferred to a PVDF membrane and subjected to protein sequencing by Edman degradation [Ausubel et al. (1987)]. Protein sequencing and HPLC analyses were carried out by the ISU Protein Facility.

REFERENCES CITED

Abraham, J., Nasmyth, K. A., Strathern, J. N., Klar, A. J. S., and Hicks, J. B. (1984). Regulation of mating-type information in yeast: negative control requiring sequences both 5' and 3' to the regulated region. J. Mol. Biol. 176, 307–331.

Andrulis, E. D., Neiman, A. M., Zappulla, D. C., Sternglanz, R. (1998) Perinuclear localization of chromatin facilitates transcriptional silencing. Nature 394, 592–595.

Ausubel, F. M., Brent, R., Kingston, R. E., Moore, D. D., Seidman, J. G., Smith, J. A., and Struhl, K. (1987) Current Protocols in Molecular Biology, Greene/Wiley Interscience, New York.

Boeke, J. D., Trueheart, J., Natsoulis, G., and Fink, G. R. (1987) 5-Fluoroorotic acid as a selective agent in yeast molecular genetics, Methods Enzymol, 154, 164–75.

Chalker, D. L., and Sandmeyer, S. B. (1993). Sites of RNA polymerase III transcription initiation and Ty3 integration at the U6 gene are positioned by the TATA box. Proc. Natl. Acad. Sci. USA 90, 4927–4931.

Chalker, D. L., and Sandmeyer, S. B. (1992). Ty3 integrates within the region of RNA polymerase III transcription initiation. Genes & Dev. 6, 117–128.

Chien, C. T., Buck, S., Sternglanz, R., and Shore, D. (1993) Targeting of SIR1 protein establishes transcriptional silencing at HM loci and telomeres in yeast, Cell, 75, 531–41.

Curcio, M. J., and Morse, R. H. (1996). Tying together integration and chromatin. Trends Genet. 12,436–438.

Devereux, J., Haeberli, P., and Smithies, O. (1984). A comprehensive set of sequence analysis programs for the VAX. Nucl. Acids Res. 12, 387–395.

Devine, S. E., and Boeke, J. D. (1996). Regionally-specific, targeted integration of the yeast retrotransposon Ty1 upstream of genes transcribed by RNA polymerase III. Genes & Dev. 10, 620–633.

Gallay, P., Hope, T., Chin, D., and Trono, D. (1997). HIV-1 infection of nondividing cells through the recognition of integrase by the importin/karyopherin pathyway. Proc. Natl. Acad. Sci. USA 94, 9825–9830.

Gottschling, D. E., Aparicio, O. M., Billington, B. L., and Zakian, V. A. (1990) Position effect at S. cerevisiae telomeres: reversible repression of Pol II transcription, Cell, 63, 751–62.

James, Genomic libraries and a host strain designed for highly efficient two-hybrid selection in yeast. Genetics, 144, 1425–1436.

Kalpana, G. V., Marmon, S., Wang, W., Crabtree, G. R., and Goff, S. P. (1994). Binding and stimulation of HIV-1 integrase by a human homolog of yeast transcription factor SNF5. Science 266,2002–2006.

Katz, R. A., and Skalka, A. M. (1994). The retroviral enzymes. Annu. Rev. Biochem. 63, 133–173.

Ke, N., and Voytas, D. F. (1997). High frequency cDNA recombination of the Saccharomyces retrotransposon Ty5: the LTR mediates formation of tandem elements. Genetics 147, 545–556.

Keeney, J. B., Chapman, K. B., Lauermann, V., Voytas, D. F., Astrom, S. U., von Pawel-Rammingen, U., Bystrom, A., and Boeke, J. D. (1995). Multiple molecular determinants for retrotransposition in a primer tRNA. Mol. Cell. Biol. 15, 217–226.

Kenna, M. A., Brachmann, C. B., Devine, S. E., and Boeke, J. D. (1998). Invading the yeast nucleus: a nuclear localization signal at the C-Terminus of Ty1 integrase is required for transposition in vivo. Mol. Cell. Biol. 18: 1115–1124.

Kimmerly, W. J., and Rine, J. (1987). Replication and segregation of plasmids containing cis-acting regulatory sites of silent mating-type genes in Saccharonyces cerevisiae are controlled by the SIR genes. Mol. Cell. Biol. 7,4225–4237.

Kirchner, J., Connolly, C. M., and Sandmeyer, S. B. (1995). Requirement of RNA polymerase III transcription factors for in vitro position-specific integration of a retroviruslike element. Science 267,1488–1491.

Laurenson, P., and Rine, J. (1992). Silencers, silencing, and heritable transcriptional states. Microbiol. Rev. 56, 543–560.

Moore, S. P., and Garfinkel, D. J. (1994). Expression and partial purification of enzymatically active recombinant Ty1 integrase in Saccharomyces cerevisiae. Proc. Natl. Acad. Sci. USA 91, 1843–1847.

Moore, S. P., Rinckel, L. A., and Garfinkel, D. J. (1998). A Ty1 integrase nuclear localization signal required for retrotransposition. Mol. Cell. Biol. 18: 1105–1114.

Palladino, F., Laroche, T., Gilson, E., Axelrod, A., Pillus, L., and Gasser, S. M. (1993). SIR3 and SIR4 proteins are required for the positioning and integrity of yeast telomeres. Cell 75, 543–555.

Sandmeyer, S. B., Hansen, L. J., and Chalker, D. L. (1990). Integration specificity of retrotransposons and retroviruses. Annu. Rev. Genet 24, 491–518.

Sharon, G., Burkett, T. J., and Garfinkel, D. J. (1994). Efficient homologous recombination of Ty1 element cDNA when integration is blocked. Mol. Cell. Biol. 14, 6540–6551.

Sikorski, R. S., and Hieter, P. (1989). A system of shuttle vectors and yeast host strains designed for efficient manipulation of DNA in Saccharomyces cerevisiae. Genetics 122, 19–27.

Thompson, J. D., Higgins, D. G., and Gibson, T. J. (1994). CLUSTAL W: improving the sensitivity of progressive multiple sequence alignment through sequence weighting, positions-specific gap penalties and weight matrix choice. Nucl. Acids Res. 22, 4673–4680.

Vinson, C. R., Sigler, P. B., and McKnight, S. L. (1989). Scissors-Grip model for DNA recognition by a family of leucine zipper proteins. Science 246, 911–916.

Wakimoto, B. (1998) Beyond the nucleosome: epigenetic aspects of position-effect variegation in Drosophila. Cell 93, 321–324.

Xiong, Y., and Eickbush, T. H. (1990). Origin and evolution of retroelements based upon their reverse transcriptase sequences. EMBO J. 9, 3353–3362.

Zou, S., Ke, N., Kim, J. M., and Voytas, D. F. (1996a). The Saccharomyces retrotransposon Ty5 integrates preferentially into regions of silent chromatin at the telomeres and mating loci. Genes & Dev. 10, 634–645.

Zou, S., Kim, J. M., and Voytas, D. F. (1996b). The Saccharomyces retrotransposon Ty5 influences the organization of chromosome ends. Nucl. Acids Res. 24, 4825–4831.

Zou, S., and Voytas, D. F. (1997). Silent chromatin determines target preference of the retrotransposon Ty5. Proc. Natl. Acad. Sci. USA 94, 7412–7416.

Zou, S., Wright, D. A., and Voytas, D. F. (1995). The Saccharomyces Ty5 retrotransposon family is associated with origins of DNA replication at the telomeres and the silent mating locus HMR. Proc. Natl. Acad. Sci. USA 92, 920–924.

TABLE 1

M3 chromosomal insertions.

| Insertion | Chromosome | Insertion site (bp) | Distance to nearest X repeat | Inside an ORF? |
|---|---|---|---|---|
| 1 | IV | 102,661 | 101 kb | Yes |
| 2 | IV | 600,371 | 599 kb | No |
| 3 | VII | 1,058,849 | 24 kb | No |
| 4 | IX | 75,575 | 67 kb | Yes |
| 5 | X | 458,368 | 296 kb | Yes |
| 6 | XI | 385,612 | 279 kb | Yes |
| 7 | XII | 451,597 | 449 kb | No |
| 8 | XIII | 904,048 | 19 kb | No |
| 9 | XIV | 335,754 | 328 kb | No |
| 10 | XIV | 719,363 | 63 kb | Yes |

| | Insertions in silent chromatin | Insertions within 1.5 kb of X repeat ACS | Insertions inside an ORF |
|---|---|---|---|
| Summary of M3 Insertions: | 0/10 | 0/10 | 5/10 |
| Summary of wt insertions on chr III[a]: | 18/19 | 18/19 | 1/19 |
| Summary of wt insertions on other chromosomes[b]: | 14/15 | 12/15 | 4/15 |

[a]Data from Zou et al., 1996a.
[b]Data from Zou et al., 1996b.

TABLE 3

Targeting mutations are limited to a stretch of 6 amino acids

| Construct | Amino Acid Sequence | Targeting to HMR plasmid | SEQ ID NO |
|---|---|---|---|
| WT | SPPSLDSSPPNTS | 7.9% | — |
| Part A: mutants found by mutation screens | | | |
| rut-3 | SPPSSDSSPPNTS | 0.7% | 7 |
| rut-15 | SPPSLDSSPLNTS | 3.0% | 8 |
| rut-31 | SPPSLDSSPQNTS | 2.0% | 9 |
| rut-38 | SPPSLDSLPPNTS | 1.1% | 10 |
| rut-41 | SPPSLDPSPPNTS | 0.7% | 11 |
| rut-46 | SPPSLDSPPPNTS | 0.6% | 12 |
| pWW39 | SPPSVDSPPPNTS | 2.0% | 13 |
| Part B: mutants created by site-directed mutagenesis | | | |
| pXW198 | APPALDSSPPNTS | 8.6% | 14 |
| pXW199 | SAPSLDSSPPNTS | 8.0% | 15 |
| pXW200 | SPASLDSSPPNTS | 8.6% | 16 |
| pXW201 | SAASLDSSPPNTS | 8.2% | 17 |
| pXW202 | SPPSLDSSPPNAA | 7.0% | 18 |
| pWW42 | SPPSLDSSPPATS | 8.0% | 19 |

In Part A, the amino acid Sequence for the WT (wild-type Ty5) corresponds to amino acids 1088 to 1100 of SEQ ID NO: 2. In Part A, the integrase sequences correspond to amino acids 1088 to 1100 of integrase, where the remaining amino acids are as given in SEQ ID NO: 2 for the wild-type Ty5 protein. The sequences given in Part B similarly are amino acids 1088 to 1100 of integrase, otherwise as given in SEQ ID NO: 2.

TABLE 2

Transposition frequency and target specificity of different Ty5 constructs.

| Construct[a] | Transposition Freq.[b] | Fold decrease | Targeting to HMR plasmid[b] | Fold decrease |
|---|---|---|---|---|
| WT | 4.37E-5 | 1.0 | 7.94% | 1.0 |
| M3 | 1.15E-5 | 3.8 | 0.35% | 22.7 |
| pXW118 | 3.43E-5 | 1.3 | 7.50% | 1.1 |
| pXW119 | 1.23E-5 | 3.6 | 0.40% | 19.9 |
| pXW138 | 4.27E-5 | 1.0 | 6.55% | 1.2 |
| pXW137 | 1.16E-5 | 3.8 | 0.46% | 17.3 |

[a]Ty5 elements are drawn schematically. Arrowheads represent the LTRs; the wild-type element is white and the M3 element is black. The region swapped in pXW118 and pXW119 represents the 2.0 kb SphI fragment. For pXW138 and pXW137, D and L represent the amino acid sequence changes at Ser1017 and Ser1094, respectively.
[b]Values represent the average of results obtained from three independent transformants.

TABLE 4

| INFORMATION FOR SEQ ID NO:1: |
| --- |

(i)  SEQUENCE CHARACTERISTICS:
     (A) LENGTH: 6660 base pairs
     (B) TYPE: nucleic acid
     (C) STRANDEDNESS: double
     (D) TOPOLOGY: not relevant (ii) MOLECULE TYPE: DNA (genomic)

(iii) HYPOTHETICAL: NO (iv) ANTI-SENSE: NO (vi) ORIGINAL SOURCE:
     (A) ORGANISM: Saccharomyces paradoxus
     (B) STRAIN: NRRL Y-17217

(ix) FEATURE:
     (A) NAME/KEY: CDS
     (B) LOCATION: 1441..6321

(ix) FEATURE:
     (A) NAME/KEY: misc_feature
     (B) LOCATION: 1228..6602
     (D) OTHER INFORMATION: /function= "retrotransposon"
     /product= "Ty5-6p"

(ix) FEATURE:
     (A) NAME/KEY: misc_feature
     (B) LOCATION: 1228..1478
     (D) OTHER INFORMATION: /function= "5' LTR of Ty5-6p"

(ix) FEATURE:
     (A) NAME/KEY: misc_feature
     (B) LOCATION: 6352..6602
     (D) OTHER INFORMATION: /function= "3' LTR of Ty5-6p"

(ix) FEATURE:
     (A) NAME/KEY: misc_feature
     (B) LOCATION: 2852..4827
     (D) OTHER INFORMATION: /function= "integrase region coding
     region of Ty5-6p"

(xi) SEQUENCE DESCRIPTION: SEQ ID NO:1:

```
GGGACAACCC CCCAACGCCA ATAAACATCG TTCCTCATCC TCAGAAAAAC GTACACTCCT        60

CATCATAAAC TTCATATAGT TACAATTATG ACTATGTATG AAATTTTGTA GCGCCCCTGT       120

TTCTTGGGGA TCTACAAATC AATCAACCAG CTCGTAATTG TGTGAGAACC GATTGCTGAT       180

TCTGCGCATT TATGCATAAT TATTGTCCTC CAGTAGTTGC CTTGGTTTGG TTATGCAGGA       240

ATTTTCAGTA GTCATTTTTT TAAGCAACAA ATGACTAAAA CCTACACATG TTTCTTAGAC       300

AAAGTACATA CGCAAATAAG ATAGCAGACA AAGCATTAAT ATAATAACAA GTCCTTGTTA       360

TTCTTATTTT TATCGTCCTT TTTCTGTTTT CCGCTCGGGT GACGCAGTT CAAATCTCTT        420

CCTTTGGCGG TTGATTCAGT AATTCTTCAA TTATTTGAGA GAGTCCTAAC GGCCTAGTCA       480

TGCATGAGAA TCTTTTAACC ACCTTCCCAT TTCGGTCTAT CAAAAACTTT TCAAAATTCC       540

ACTTTATCAT TTTTATTCCA GATTTCCCGC TCACTGAGTT TTTTAAGAAC TTGTAGACAG       600

GATCTTGCTT TTGCCCATTA CAACGGATCT TATGTAGGAT AGGGAAGGTC ACACCGAATT       660

TATTCTGACA AAACTTATTG ATCTCCTCAT CCTTCTCAAA CTCTTGATTT CCAAATTGAC       720

CGCAAGGAAA GGCCCGATCA TCAGACCATG TGATTTGTAT TTTTCGTACA AGTACTCTAA       780

TTCCTTATAT TGTGGTGTGA ATGCACCATG AGATGCTACA TTAACTATCA GTACCACTTT       840

GTTACGCAAG GAGCTAAAGG GGAATGGATT TCCATCTTCA TCTATGGGCG CAAAAGAATA       900

AAATTCTTGC ATCGAAACTT ATATAGTGTT CCTTGGTTGA TGTTCCTTGT GCCGAATTAC       960

GATTAGAGAA ACTCGCTGTG CACAATACCA CCTACATGAC TAAATTCTGT CTGTACACTA      1020
```

TABLE 4-continued

INFORMATION FOR SEQ ID NO:1:

```
CTTACTGTAT TATATAATCA CTGTAGATGT GTTAACTGTA AGCACTCTCT GTAGCAAAGG         1080

TGAGTCCGGA TTTAAGCACT TATGGACGTG GCAAACGAGG GATGACTCGC TTACCCTATA         1140

AAAATAGGGA ACAGAAGGGG AAAAGGAACT ACGGAGAAGT TCCACATGAA GACGGTAGTG         1200

GGGAATGTCG AGGGGATAC TGTCGTATGT TGAATGTGAT AACCCAAAAG CATGATATGG          1260

GTAATGTTTC AGTACTGTTT CAGAATTGTT TCAGTAATGT TTTAGACAAG GAAAACATAG         1320

AGCAGCAAAC CTCCGATCCG ACAGTACTTA AGAAACCATA GTTTCTGTGT ACAAGAGTAG         1380

TACCTATGTA ATTCTTACAT TTACATAACA TATAGAAAGG TCCAATAAAC TTACAACATT         1440
```

| | | | | | | | | | | | | | | | | |
|---|---|---|---|---|---|---|---|---|---|---|---|---|---|---|---|---|
| ATG | ACA | TAT | AAG | CTA | GAT | CGT | AAT | TCA | CTA | CGT | CAA | CAG | GTT | ATG | AGC | 1488 |
| Met | Thr | Tyr | Lys | Leu | Asp | Arg | Asn | Ser | Leu | Arg | Gln | Gln | Val | Met | Ser | |
| 1 | | | | 5 | | | | | 10 | | | | | 15 | | |

```
CCT GAG AGC AAT GCT TCA GAG ACC ATA ATT AAT CTA TCT AAT CCC AAC          1536
Pro Glu Ser Asn Ala Ser Glu Thr Ile Ile Asn Leu Ser Asn Pro Asn
             20                  25                  30

AAT TAT AAA CAG TGG CTG TAC GGT ATC GAG ACC GCT GCT GAA TAT GCT          1584
Asn Tyr Lys Gln Trp Leu Tyr Gly Ile Glu Thr Ala Ala Glu Tyr Ala
         35                  40                  45

AAC GAA TAT ATG AAC GAA TTC GTT CAT ACC GGA GAT ATC CAA TCA ATG          1632
Asn Glu Tyr Met Asn Glu Phe Val His Thr Gly Asp Ile Gln Ser Met
     50                  55                  60

AAA AGG GAT TAC AAT CTC AGC GCG AAT GAT GAA AGC TTT GTC AAA ACC          1680
Lys Arg Asp Tyr Asn Leu Ser Ala Asn Asp Glu Ser Phe Val Lys Thr
 65                  70                  75                  80

GTA TTT AAC AGT TTC CTG GTA AAG CTC TAC AAG AAA ACT ATC GTG GGT          1728
Val Phe Asn Ser Phe Leu Val Lys Leu Tyr Lys Lys Thr Ile Val Gly
                 85                  90                  95

GAA GCT GCA TGT GAA ATG AAC TGG ATA TGT GAT GAT TCA CTT GGA AGG          1776
Glu Ala Ala Cys Glu Met Asn Trp Ile Cya Asp Asp Ser Leu Gly Arg
             100                 105                 110

GTC TCT GCT TAT GAT ATT TTC TCG CAC TTC GAA GAA AAC TAT AAT GAA          1824
Val Ser Ala Tyr AsP Ile Phe Ser His Phe Glu Glu Asn Tyr Asn Glu
         115                 120                 125

GTC ACT ATT GGA TCC AGG CTT ACT CTT ATA GAG GAC TTA CCA AAT ATA          1872
Val Thr Ile Gly Ser Arg Leu Thr Leu Ile Glu Asp Leu Pro Asn Ile
     130                 135                 140

TCC TCC AAG CCT GTA GAT GAA ATC GCT TCC TTT TTG AAA ACC CTA TTC          1920
Ser Ser Lys Pro Val Asp Glu Ile Ala Ser Phe Leu Lys Thr Leu Phe
145                 150                 155                 160

ACA ATG CTT GAA GAC AAT AGC GAA GAA CAG GAC AAA AAG AAA AGA CGC          1968
Thr Met Leu Glu Asp Asn Ser Glu Glu Gln Asp Lys Lys Lys Arg Arg
                 165                 170                 175

GAT ACC AAT ATC GCG TTG CTA TTA ATG ACC TTC TTA CCC GAG TTA AAG          2016
Asp Thr Asn Ile Ala Leu Leu Leu Met Thr Phe Leu Pro Glu Leu Lys
             180                 185                 190

GAA TCA TTC CAC GAG AAA TTC GGT GAC TCT AAA GCT CTT CAG CTG TCA          2064
Glu Ser Phe His Glu Lys Phe Gly Asp Ser Lys Ala Leu Gln Leu Ser
         195                 200                 205

CAA GTC ATT AGA TTC TGT AAA TTA AAG GCG TCA TCG AAT TCA TTA TCT          2112
Gln Val Ile Arg Phe Cys Lys Leu Lys Ala Ser Ser Asn Ser Leu Ser
     210                 215                 220

TCA GTC TCA GAT ACA TTG GTT GCA CAA GAC AGA AGA AGC TAT CAA AAG          2160
Ser Val Ser Asp Thr Leu VaL Ala Gln Asp Arg Arg Ser Tyr Gln Lys
225                 230                 235                 240

AAA GGA AAT AAG GGA TGT ATG ATT TGT GGG GCA GAT CAT CGC TTA AGC          2208
Lys Gly Asn Lys Gly Cys Met Ile Cys Gly Ala Asp His Arg Leu Ser
                 245                 250                 255
```

TABLE 4-continued

INFORMATION FOR SEQ ID NO:1:

| | |
|---|---|
| AAC TGT TCT CTG CTT AAA AGA AGA ATA CCA GAA GCC AGA ATC TTT AAA<br>Asn Cys Ser Leu Leu Lys Arg Arg Ile Pro Glu Ala Arg Ile Phe Lys<br>                260                 265                 270 | 2256 |
| TTA TAT CCT AAT GAC AAG ACG AAT AGA TCT TCA TCT GCT AGT GTT GCG<br>Leu Tyr Pro Asn Asp Lys Thr Asn Arg Ser Ser Ser Ala Ser Val Ala<br>                    275                 280                 285 | 2304 |
| ATT CCT GAC TAT GAA ACG CAA GGC CAA ACA GCA GGA CAG ATA ACA CCA<br>Ile Pro Asp Tyr Glu Thr Gln Gly Gln Thr Ala Gly Gln Ile Thr Pro<br>        290                 295                 300 | 2352 |
| AAG TCC TGG CTC TGT ATG TTA TCT TCG ACC GTC CCA GCT ACC AAA TCC<br>Lys Ser Trp Leu Cys Met Leu Ser Ser Thr Val Pro Ala Thr Lys Ser<br>305                 310                 315                 320 | 2400 |
| TCA GAT TGG ATT TGT GAC ACA GGA TGT ACT TCA CAC ATG TGC CAC GAC<br>Ser Asp Trp Ile Cys Asp Thr Gly Cys Thr Ser His Met Cys His Asp<br>                    325                 330                 335 | 2448 |
| CGT TCT ATG TTC TCA TCA TTT ACT AGA TCC TCT AAG AAA GAC TTT GTC<br>Arg Ser Met Phe Ser Ser Phe Thr Arg Ser Ser Lys Lys Asp Phe Val<br>                340                 345                 350 | 2496 |
| AGA GGA GTC GGC GGT TCC ATA CCC ATC ATG GGC TCC GGG ACT GTA AAC<br>Arg Gly Val Gly Gly Ser Ile Pro Ile Met Gly Ser Gly Thr Val Asn<br>            355                 360                 365 | 2544 |
| ATC GGC ACT GTT CAA TTA AAT GAC GTA TCC TAC GTC CCT GAT TTA CCA<br>Ile Gly Thr Val Gln Leu Asn Asp Val Ser Tyr Val Pro Asp LeU Pro<br>370                 375                 380 | 2592 |
| GTC AAC CTA ATA TCC ATT TGG AAA CTA TGT GCT AAA TCC AAC TCT TCT<br>Val Asn Leu Ile Ser Ile Trp Lys Leu Cys Ala Lys Ser Asn Ser Ser<br>385                 390                 395                 400 | 2640 |
| GTT ACG TTC ACA AAA GAG GGT GTC ACT GTG AAA TCA CCT GAT GAC GTG<br>Val Thr Phe Thr Lys Glu Gly Val Thr Val Lys Ser Pro Asp Asp Val<br>                    405                 410                 415 | 2688 |
| ATT TCT ACG GCT GGG AAG TTA AAC AAT TAT CTG TAC ATT TTC GAT GAT<br>Ile Ser Thr Ala Gly Lys Leu Asn Asn Tyr Leu Tyr Ile Phe Asp Asp<br>                420                 425                 430 | 2736 |
| CTT ACG CCC GTA ACT ACC TTC TCT TCG CAA AAT TAC TTC TGC TCT AAA<br>Leu Thr Pro Val Thr Thr Phe Ser Ser Gln Asn Tyr Phe Cys Ser Lys<br>            435                 440                 445 | 2784 |
| ACA TTG GAT TCA TCT AAA ATG ATA ACT TCC GCA GCG TTT CAT ACC GTT<br>Thr Leu Asp Ser Ser Lys Met Ile Thr Ser Ala Ala Phe His Thr Val<br>        450                 455                 460 | 2832 |
| GCA GAT AAA ATG TTG TCG CAA CAC ATT TCT CCC ACT GCT CTC CCG GTA<br>Ala Asp Lys Met Leu Ser Gln His Ile Ser Pro Thr Ala Leu Pro Val<br>465                 470                 475                 480 | 2880 |
| AAA TGG CAT GCT CGT ATG GGC CAT CCC GGA GCA GAT ATT TAC AAT TCC<br>Lys Trp His Ala Arg Met Gly His Pro Gly Ala Asp Ile Tyr Asn Ser<br>                    485                 490                 495 | 2928 |
| TTG GCT AGA ACT CTG CGT TTT CCA AAA TTT AAG ACG GCT GAA TAC ACT<br>Leu Ala Arg Thr Leu Arg Phe Pro Lys Phe Lys Thr Ala Glu Tyr Thr<br>                500                 505                 510 | 2976 |
| ATT TGT CCT ACC TGC TCA CTA GCA AAA GGA ATC ATC AAA AAG GGT AAA<br>Ile Cys Pro Thr Cys Ser Leu Ala Lys Gly Ile Ile Lys Lys Gly Lys<br>            515                 520                 525 | 3024 |
| GTC TCG CTC AAA AAA TAT ACC CAA AAT ATT CAA ATG GTA CAG GCT GAT<br>Val Ser Leu Lys Lys Tyr Thr Gln Pro Leu Gln Met Val Gln Ala Asp<br>        530                 535                 540 | 3072 |
| CTC TGT GGT GGG TTT CGC TAC CAA GAG TTT CAG TCA AAT AAA TAT TTT<br>Leu Cys Gly Gly Phe Arg Tyr Gln Glu Phe Gln Ser Asn Lys Tyr Phe<br>545                 550                 555                 560 | 3120 |

TABLE 4-continued

INFORMATION FOR SEQ ID NO:1:

| | |
|---|---|
| CTT ACT ATC CGT GAT GCC TAT AGT CGC TAC TAC TCT GTA ATA CAT TTA<br>Leu Thr Ile Arg Asp Ala Tyr Ser Arg Tyr Tyr Ser Val Ile His Leu<br>565 570 575 | 3168 |
| AAA TCC AAA GCA GAC GCT CCG ATA AAA TTC ATG GAA TGG ATC AAC GAA<br>Lys Ser Lys Ala Asp Ala Pro Ile Lys Phe Met Glu Trp Ile Asn Glu<br>580 585 590 | 3216 |
| ACC GAA CAA TAC TTT AGC TCC CGG GGT GGA TTC AAA GTC GGA TCT GTT<br>Thr Glu Gln Tyr Phe Ser Ser Arg Gly Gly Phe Lys Val Gly Ser Val<br>595 600 605 | 3264 |
| CGT ACA GAC AAT GGT ACA GAA TTC GTA AAT AAA AAT CTT CAT GCG TTT<br>Arg Thr Asp Asn Gly Thr Glu Phe Val Asn Lys Asn Leu His Ala Phe<br>610 615 620 | 3312 |
| TTT AAA TCT AAA GGA ATA GAG CAT CAG TTA ACT ATT CCA TAT CAT AGT<br>Phe Lys Ser Lys Gly Ile Glu His Gln Leu Thr Ile Pro Tyr His Ser<br>625 630 635 640 | 3360 |
| TAT CAA AAT GGT GCT GTT GAA CGT GCA CAT CGT ACC ATC GAA GAA CGC<br>Tyr Gln Asn Gly Ala Val Glu Arg Ala His Arg Thr Ile Glu Glu Arg<br>645 650 655 | 3408 |
| ACT CGT TGT CTC CTT ATC GGG GGG CGT GTT CCT CCG TCC TTG TGG TCT<br>Thr Arg Cys Leu Leu Ile Gly Gly Arg Val Pro Pro Ser Leu Trp Ser<br>660 665 670 | 3456 |
| GAA GCT GTT TCT TGC GCA GTC TAT TTA ATC AAT AGG TCC CCT GTA GTG<br>Glu Ala Val Ser Cys Ala Val Tyr Leu Ile Asn Arg Ser Pro Val Val<br>675 680 685 | 3504 |
| TCC AAA AAT AAC AGT ATC CCA TAC TGC CGG TGG TTC AAC ATC CCC GCA<br>Ser Lys Asn Asn Ser Ile Pro Tyr Cys Arg Trp Phe Asn Ile Pro Ala<br>690 695 700 | 3552 |
| AAA GAT TTC GGT ATC GCA CAT CTT CGA ATT TTT GGA TGT ACA GCA TAC<br>Lys Asp Phe Gly Ile Ala His Leu Arg Ile Phe Gly Cys Thr Ala Tyr<br>705 710 715 720 | 3600 |
| GCA ACC TTA CAA CCT AGT CTT CGA GAC GGC AAA CTT GCC CCA ACT GTC<br>Ala Thr Leu Gln Pro Ser Leu Arg Asp Gly Lys Leu Ala Pro Thr Val<br>725 730 735 | 3648 |
| ATA TCT GGT GTT ATG GTT GGC TAT GAC TCT AAC CAT CGA GGA TAC AGG<br>Ile Ser Gly Val Met Val Gly Tyr Asp Ser Asn His Arg Gly Tyr Arg<br>740 745 750 | 3696 |
| ATT TAT CAT CCC GAA ACT GGC CGC ATC TTT GTG AGC AGT CAA GTT CGA<br>Ile Tyr His Pro Glu Thr Gly Arg Ile Phe Val Ser Ser Gln Val Arg<br>755 760 765 | 3744 |
| TTT GAC GAA CAC ATG TTT CCT CTT GCT GAT ACA GAG GCA GTT CAC GTC<br>Phe Asp Glu His Met Phe Pro Leu Ala Asp Thr Glu Ala Val His Val<br>770 775 780 | 3792 |
| TCT CAC GAC TTT GCC ACT TCC GCT ATT GGG GGG GTG TCC AAA TAT CCT<br>Ser His Asp Phe Ala Thr Ser Ala Ile Gly Gly Val Ser Lys Tyr Pro<br>785 790 795 800 | 3840 |
| GAA ACA GGG TCA ACC GTC TCT GCT CCA AAG AAC GAC GGA TCT GAC TTG<br>Glu Thr Gly Ser Thr Val Ser Ala Pro Lys Asn Asp Gly Ser Asp Leu<br>805 810 815 | 3888 |
| GCA AAT TTG CCA ATA ACT GTT CCC AAA AAT GTA AAT CAA CCA GCA CAT<br>Ala Asn Leu Pro Ile Thr Val Pro Lys Asn Val Asn Gln Pro Ala His<br>820 825 830 | 3936 |
| AAA CCT AAT ACC AGT AAC ATC TCT TCC TCT GAT GAT GAT GAG GAT ATT<br>Lys Pro Asn Thr Ser Asn Ile Ser Ser Ser Asp Asp Asp Glu Asp Ile<br>835 840 845 | 3984 |
| TCA ATG GAA ATC GAA ATG GAA AAA CCT ATC CCT GAG TGT AAC CAA GAC<br>Ser Met Glu Ile Glu Met Glu Lys Pro Ile Pro Glu Cys Asn Gln Asp<br>850 855 860 | 4032 |
| AAC TTA CCA AAC TCC GGA TGT CCA CCA ACA AGG ATA CAA CAT TCT AAC | 4080 |

TABLE 4-continued

INFORMATION FOR SEQ ID NO:1:

| | |
|---|---|
| Asn Leu Pro Asn Ser Gly Cys Pro Pro Thr Arg Ile Gln His Ser Asn<br>865                      870                      875                    880 | |
| TTT GAA TCC TTA CCA ACC GTG TCT ACC GAA GAC GAA ACT AAT TCT TCT<br>Phe Glu Ser Leu Pro Thr Val Ser Thr Glu Asp Glu Thr Asn Ser Ser<br>                  885                      890                    895 | 4128 |
| ATG GAG AAA ACT CCT GAA AGA GTT CCA GCG GCA CTA ACT TAT CGA GAA<br>Met Glu Lys Thr Pro Glu Arg Val Pro Ala Ala Leu Thr Tyr Arg Glu<br>              900                      905                    910 | 4176 |
| ATT CCA AAA TCA TCC GAT TCA GAA TAT ATT CCG ACA TGC CGA AAT AGA<br>Ile Pro Lys Ser Ser Asp Ser Glu Tyr Ile Pro Thr Cys Arg Asn Arg<br>            915                      920                    925 | 4224 |
| ACT AGA CGT GTT AAA AGA ACT AAT AAG AAA CCA ACG CGA TCC CGC GAA<br>Thr Arg Arg Val Lys Arg Thr Asn Lys Lys Pro Thr Arg Ser Arg Glu<br>930                      935                      940 | 4272 |
| ATA GAA ATA TAT GAT ATA TCA CGT CCA AAC GTA ATA TCG AGT GAC AAC<br>Ile Glu Ile Tyr Asp Ile Ser Arg Pro Asn Val Ile Ser Ser Asp Asn<br>945                      950                      955                    960 | 4320 |
| TTA CCT GAA GTT AGA AGT GCC AAG CAA AGA AAG ACG GTG TCC AAT ACA<br>Leu Pro Glu Val Arg Ser Ala Lys Gln Arg Lys Thr Val Ser Asn Thr<br>            965                      970                    975 | 4368 |
| AAT GAT ACT GTA GCA AGG ACA AAT AGA CTT CCA ACC GTG CTA CGA ACT<br>Asn Asp Thr Val Ala Arg Thr Asn Arg Leu Pro Thr Val Leu Arg Thr<br>            980                      985                    990 | 4416 |
| CTA GAC TCA AAC AAC ATT GAC ACG CTG CAT GTT GCC AGT ACT GGT GAA<br>Leu Asp Ser Asn Asn Ile Asp Thr Leu His Val Ala Ser Thr Gly Glu<br>            995                      1000                  1005 | 4464 |
| GAA GTG TCC ATC GAA AGA CTT TCA AGC ATG GCT CTT CAG GAA GCG AAG<br>Glu Val Ser Ile Glu Arg Leu Ser Ser Met Ala Leu Gln Glu Ala Lys<br>          1010                      1015                    1020 | 4512 |
| AAC AAT TCC GCC AGA ACT AAT CAA GCT AAT TCT CTT ACT GAT TGG TTT<br>Asn Asn Ser Ala Arg Thr Asn Gln Ala Asn Ser Leu Thr Asp Trp Phe<br>1025                      1030                    1035                    1040 | 4560 |
| CCA GTA GGC GCA ATG CCG ATA CCT GAC CAG AGG TAT CTA TCC GTT CAC<br>Pro Val Gly Ala Met Pro Ile Pro Asp Gln Arg Tyr Leu Ser Val His<br>                    1045                    1050                    1055 | 4608 |
| GAT GGA ACA TAT ATC AGC GAC TCA CAA GAT GTG GGT GAT ACT GAC CTC<br>Asp Gly Thr Tyr Ile Ser Asp Ser Gln Asp Val Gly Asp Thr Asp Leu<br>              1060                    1065                    1070 | 4656 |
| ACT CCT GCT GTA ACC AGG CTA GTT ACT GAA GAG AAT TCA ATC GAA TCT<br>Thr Pro Ala Val Thr Arg Leu Val Thr Glu Glu Asn Ser Ile Glu Ser<br>          1075                      1080                    1085 | 4704 |
| CCT CCA TCG TTG GAT TCA TCG CCT CCA AAT ACC TCA TTT AAC GCG GCT<br>Pro Pro Ser Leu Asp Ser Ser Pro Pro Asn Thr Ser Phe Asn Ala Ala<br>            1090                      1095                    1100 | 4752 |
| CTA ACT GCT ATT ATC CAT AGC ACA AAA AAA GGA AAC CCG AAA ACC TAT<br>Leu Thr Ala Ile Ile His Ser Thr Lys Lys Gly Asn Pro Lys Thr Tyr<br>1105                      1110                    1115                    1120 | 4800 |
| GCC CAA GCA ATG GGA AGG CCT GAC TTT CAA GAA TGG CAC AAC GCA TGC<br>Ala Gln Ala Met Gly Arg Pro Asp Phe Gln Glu Trp His Asn Ala Cys<br>              1125                    1130                    1135 | 4848 |
| CTC AAG GAA CTT TCC GCG TTC AAA GAT CAC AAT ACG TAC AAA TTG GTG<br>Leu Lys Glu Leu Ser Ala Phe Lys Asp His Asn Thr Tyr Lys Leu Val<br>          1140                      1145                    1150 | 4896 |
| TCT CTT CCA AAG CAA AGA AGA GCT CTT GGA TCG CGC TGG GTA TTC ACA<br>Ser Leu Pro Lys Gln Arg Arg Ala Leu Gly Ser Arg Trp Val Phe Thr<br>            1155                      1160                    1165 | 4944 |
| ATA AAA GAC TCC GGG ACG TAC AAA GCT CGC CTT GTC GCC CAA GGA CAT<br>Ile Lys Asp Ser Gly Thr Tyr Lys Ala Arg Leu Val Ala Gln Gly His | 4992 |

TABLE 4-continued

INFORMATION FOR SEQ ID NO:1:

```
       1170                 1175                 1180
ACT CAA AAG GCT GGT ATT GAC TAT CAA GAA ACT TTT GCA CCA GTC ATT        5040
Thr Gln Lys Ala Gly Ile Asp Tyr Gln Glu Thr Phe Ala Pro Val Ile
1185                 1190                 1195                 1200

CGA TAT GAC TCT GTT AGA TTA TTT CTG GCC CTT GCT AGC TGC CTC AAA        5088
Arg Tyr Asp Ser Val Arg Leu Phe Leu Ala Leu Ala Ser Cys Leu Lys
                1205                 1210                 1215

CTA ATA GTA TAT CAG ATG GAC GTT GAC ACC GCG TTT CTA AAC TCA AAA        5136
Leu Ile Val Tyr Gln MeT Asp Val Asp Thr Ala Phe Leu Asn Ser Lys
           1220                 1225                 1230

ATG AAT GAG CCG GTA TAC GTA AAA CAA CCA CCC GGA TTT ATT AAT GAA        5184
Met Asn Glu Pro Val Tyr Val Lys Gln Pro Pro Gly Phe Ile Asn Glu
      1235                 1240                 1245

AGT AAT CCC GAC TAT GTA TGG GAA CTA TAC GGC GGT ATG TAT GGA CTC        5232
Ser Asn Pro Asp Tyr Val Trp Glu Leu Tyr Gly Gly Met Tyr Gly Leu
 1250                 1255                 1260

AAG CAA GCC CCA TTA CTA TCC AAC GAA CAT ATC AAC AAT ACT CTT CAA        5280
Lys Gln Ala Pro Leu Leu Trp Asn Glu His Ile Asn Asn Thr Leu Gln
1265                 1270                 1275                 1280

AAG ATT GGT TTT CGT CGA CAT GAA GGC GAA CAT GGC TTA TAC TTT CGT        5328
Lys Ile Gly Phe Arg Arg His Glu Gly Glu His Gly Leu Tyr Phe Arg
                1285                 1290                 1295

TCC ACA TCT GAT GGT CCC ATC TAC ATT GCC CTA TAC GTA GAC GAC TTA        5376
Ser Thr Ser Asp Gly Pro Ile Tyr Ile Ala Leu Tyr Val Asp Asp Leu
           1300                 1305                 1310

CTT GTT GCT GCT CCC TCT CCG AAA ATA TAT GAC AGG GTT AAG CAG AAA        5424
Leu Val Ala Ala Pro Ser Pro Lys Ile Tyr Asp Arg Val Lys Gln Lys
      1315                 1320                 1325

CTA ACG AAG TTA TAC TCA ATG AAG GAT CTA GGT AAA GTT GAC AAA TTC        5472
Leu Thr Lys Leu Tyr Ser Met Lys Asp Leu Gly Lys Val Asp Lys Phe
 1330                 1335                 1340

CTC GGT CTT AAC ATT AAT CAA TTT TCA AAT GGA GAC ATC ACT CTC TCA        5520
Leu Gly Leu Asn Ile Asn Gln Phe Ser Asn Gly Asp Ile Thr Leu Ser
1345                 1350                 1355                 1360

CTT CAA GAC TAT ATT GCT AAA GCT GCA TCT GAA AGC GAA ATA AAC ATA        5568
Leu Gln Asp Tyr Ile Ala Lys Ala Ala Ser Glu Ser Glu Ile Asn Ile
                1365                 1370                 1375

TGT AAG CCT ACA CAG ACT CCG CTC TGT GAC TCA AAG CCT CTT TTC GAA        5616
Cys Lys Pro Thr Gln Thr Pro Leu Cys Asp Ser Lys Pro Leu Phe Glu
           1380                 1385                 1390

ACA ACT TCC CCG CAC CTA AAG GAC ATC ACT CCT TAT CAG AGC ATA GTT        5664
Thr Thr Ser Pro His Leu Lys Asp Ile Thr Pro Tyr Gln Ser Ile Val
      1395                 1400                 1405

GGA CAG CTT CTC TTT TGT GCA AAT ACT GGT CGT CCT GAC ATA TCT TAT        5712
Gly Gln Leu Leu Phe Cys Ala Asn Thr Gly Arg Pro Asp Ile Ser Tyr
 1410                 1415                 1420

CCG GTC TCA CTA CTC TCC AGG TTT CTT CGC GAA CCT CGC GCA ATC CAT        5760
Pro Val Ser Leu Leu Ser Arg Phe Leu Arg Glu Pro Arg Ala Ile His
1425                 1430                 1435                 1440

TTG GAG TCT GCT CGA CGA GTT CTA CGG TAC CTA TAT ACC ACC AGA AGT        5808
Leu Glu Ser Ala Arg Arg Val Leu Arg Tyr Leu Tyr Thr Thr Arg Ser
                1445                 1450                 1455

ATG TGT CTC AAG TAT CGT TCT GGA TCT CTG TTG GCA CTA ACT GTA TAT        5856
Met Cys Leu Lys Tyr Arg Ser Gly Ser Leu Leu Ala Leu Thr Val Tyr
           1460                 1465                 1470

TGT GAT GCA TCT CAT GGA GCA ATT CAC GAT CTC CCA CAC TCT ACT GGG        5904
Cys Asp Ala Ser His Gly Ala Ile His Asp Leu Pro His Ser Thr Gly
      1475                 1480                 1485
```

TABLE 4-continued

INFORMATION FOR SEQ ID NO:1:

| | |
|---|---|
| GGG TAC GTG ACT CTA CTT GCT GGT GCT CCA GTT ACG TGG TCA TCA AAG<br>Gly Tyr Val Thr Leu Leu Ala Gly Ala Pro Val Thr Trp Ser Ser Lys<br>     1490                 1495                 1500 | 5952 |
| AAA CTC AAG GGT GTG ATT CCT GTA TCA TCT ACT GAG GCA GAA TAC ATT<br>Lys Leu Lys Gly Val Ile Pro Val Ser Ser Thr Glu Ala Glu Tyr Ile<br>1505                 1510                 1515                 1520 | 6000 |
| ACT GCA AGT GAA ACT GTC ATG GAG ATA GAA TGG ATT CAA AAC TTG TTT<br>Thr Ala Ser Glu Thr Val Met Glu Ile Glu Trp Ile Gln Asn Leu Phe<br>     1525                 1530                 1535 | 6048 |
| GAA CAC TTA GGC CAG CCA CTT ATC TCA TCA ACA TTA TAC GTA GAT AAT<br>Glu His Leu Gly Gln Pro Leu Ile Ser Ser Thr Leu Tyr Val Asp Asn<br>          1540                 1545                 1550 | 6096 |
| GAA CCT GCT ATA AAA CTA TCT AAA CAT CCT GTA TTT CAC ACG AGA ACA<br>Glu Pro Ala Ile Lys Leu Ser Lys His Pro Val Phe His Thr Arg Thr<br>     1555                 1560                 1565 | 6144 |
| AAA CAC ATT GCC TTG AGA TAT CAC AAG CTA AGA AGT GCA GTG GCA GCA<br>Lys His Ile Ala Leu Arg Tyr His Lys Leu Arg Ser Ala Val Ala Ala<br>     1570                 1575                 1580 | 6192 |
| GGC ATA ATT ACC ATA GAG CAT GTT ATT ACA AAG AGA CAA GTT GCT GAC<br>Gly Ile Ile Thr Ile Glu His Val Ile Thr Lys Arg Gln Val Ala Asp<br>1585                 1590                 1595                 1600 | 6240 |
| ATA TTT ACA AAA ATC CTT CCA GCA GAA TCA TTC AAA GCA CAT AGG GCT<br>Ile Phe Thr Lys Ile Leu Pro Ala Glu Ser Phe Lys Ala His Arg Ala<br>          1605                 1610                 1615 | 6288 |
| GTC ATG GTG AGG GAA CCA GAA ACT GCA AAA TAA CCACTCTCAT GCGTATTCAG<br>Val Met Val Arg Glu Pro Glu Thr Ala Lys *<br>          1620                 1625 | 6341 |
| TTATGGGGGG ATGTTGAATG TGATAACCCA AAAGCATGAT ATGGGTAATG TTTCAGTACT | 6401 |
| GTTTCAGAAT TGTTTCAGTA ATGTTTTAGA CAAGGAAAAC ATAGAGCAGC AAACCTCCGA | 6461 |
| TCCGACAGTA CTTAAGAAAC CATAGTTTCT GTGTACAAGA GTAGTACCTA TGTAATTCTT | 6521 |
| ACATTTACAT AACATATAGA AAGGTCCAAT AAACTTACAA CATTATGACA TATAAGCTAG | 6581 |
| ATCGTAATTC ACTACGTCAA CATCGTACAC TTAAAATATA TGTATGTATC TGCACTATTT | 6641 |
| AGTCTTGTTT TATTGGGTG | 6660 |

SEQUENCE LISTING

<160> NUMBER OF SEQ ID NOS: 26

<210> SEQ ID NO 1
<211> LENGTH: 6660
<212> TYPE: DNA
<213> ORGANISM: Saccharomyces paradoxus
<220> FEATURE:
<221> NAME/KEY: CDS
<222> LOCATION: (1441)..(6318)

<400> SEQUENCE: 1

| | |
|---|---|
| gggacaaccc cccaacgcca ataaacatcg ttcctcatcc tcagaaaaac gtacactcct | 60 |
| catcataaac ttcatatagt tacaattatg actatgtatg aaattttgta gcgcccctgt | 120 |
| ttcttgggga tctacaaatc aatcaaccag ctcgtaattg tgtgagaacc gattgctgat | 180 |
| tctgcgcatt tatgcataat tattgtcctc cagtagttgc cttggtttgg ttatgcagga | 240 |

```
                                                      -continued attttcagta gtcattttt  taagcaacaa atgacttaaa cctacacatg tttcttagac    300
aaagtacata cgcaaataag atagcagaca aagcattaat ataataacaa gtccttgtta    360
ttcttatttt tatcgtcctt tttctgtttt ccgctcgggt gacgacagtt caaatctctt    420
cctttggcgg ttgattcagt aattcttcaa ttatttgaga gagtcctaac ggcctagtca    480
tgcatgagaa tcttttaacc accttcccat ttcggtctat caaaaacttt tcaaaattcc    540
actttatcat ttttattcca gatttcccgc tcactgagtt ttttaagaac ttgtagacag    600
gatcttgctt tgcccattta caacggatct tatgtaggat agggaaggtc acaccgaatt    660
tattctgaca aaacttattg atctcctcat ccttctcaaa ctcttgatt  ccaaattgac    720 cgcaaggaaa ggcccgatca tcagaccatg tgatttgtat ttttcgtaca agtactctaa    780
ttccttatat tgtggtgtga atgcaccatg agatgctaca ttaactatca gtaccacttt    840
gttacgcaag gagctaaagg ggaatggatt tccatcttca tctatgggcg caaaagaata    900
aaattcttgc atcgaaactt atatagtgtt ccttggttga tgttccttgt gccgaattac    960
gattagagaa actcgctgtg cacaatacca cctacatgac taaattctgt ctgtacacta   1020
cttactgtat tatataatca ctgtagatgt gttaactgta agcactctct gtagcaaagg   1080
tgagtccgga tttaagcact tatggacgtg gcaaacgagg gatgactcgc ttaccctata   1140 aaataggga  acagaagggg aaaaggaact acggagaagt tccacatgaa gacgtagtg    1200 gggaatgtcg aggggatac  tgtcgtatgt tgaatgtgat aacccaaaag catgatatgg   1260 gtaatgttc  agtactgttt cagaattgtt tcagtaatgt tttagacaag gaaacatag    1320 agcagcaaac ctccgatccg acagtactta agaaaccata gtttctgtgt acaagagtag   1380
tacctatgta attcttacat ttacataaca tatagaaagg tccaataaac ttacaacatt   1440 atg aca tat aag cta gat cgt aat tca cta cgt caa cag gtt atg agc      1488
Met Thr Tyr Lys Leu Asp Arg Asn Ser Leu Arg Gln Gln Val Met Ser
 1               5                  10                  15 cct gag agc aat gct tca gag acc ata att aat cta tct aat ccc aac      1536
Pro Glu Ser Asn Ala Ser Glu Thr Ile Ile Asn Leu Ser Asn Pro Asn
             20                  25                  30 aat tat aaa cag tgg ctg tac ggt atc gag acc gct gct gaa tat gct      1584
Asn Tyr Lys Gln Trp Leu Tyr Gly Ile Glu Thr Ala Ala Glu Tyr Ala
         35                  40                  45 aac gaa tat atg aac gaa ttc gtt cat acc gga gat atc caa tca atg      1632
Asn Glu Tyr Met Asn Glu Phe Val His Thr Gly Asp Ile Gln Ser Met
     50                  55                  60 aaa agg gat tac aat ctc agc gcg aat gat gaa agc ttt gtc aaa acc      1680
Lys Arg Asp Tyr Asn Leu Ser Ala Asn Asp Glu Ser Phe Val Lys Thr
 65                  70                  75                  80 gta ttt aac agt ttc ctg gta aag ctc tac aag aaa act atc gtg ggt      1728
Val Phe Asn Ser Phe Leu Val Lys Leu Tyr Lys Lys Thr Ile Val Gly
                 85                  90                  95 gaa gct gca tgt gaa atg aac tgg ata tgt gat gat tca ctt gga agg      1776
Glu Ala Ala Cys Glu Met Asn Trp Ile Cys Asp Asp Ser Leu Gly Arg
            100                 105                 110 gtc tct gct tat gat att ttc tcg cac ttc gaa gaa aac tat aat gaa      1824
Val Ser Ala Tyr Asp Ile Phe Ser His Phe Glu Glu Asn Tyr Asn Glu
        115                 120                 125 gtc act att gga tcc agg ctt act ctt ata gag gac tta cca aat ata      1872
Val Thr Ile Gly Ser Arg Leu Thr Leu Ile Glu Asp Leu Pro Asn Ile
    130                 135                 140 tcc tcc aag cct gta gat gaa atc gct tcc ttt ttg aaa acc cta ttc      1920
Ser Ser Lys Pro Val Asp Glu Ile Ala Ser Phe Leu Lys Thr Leu Phe
145                 150                 155                 160
```

```
aca atg ctt gaa gac aat agc gaa gaa cag gac aaa aag aaa aga cgc    1968
Thr Met Leu Glu Asp Asn Ser Glu Glu Gln Asp Lys Lys Lys Arg Arg
            165                 170                 175 gat acc aat atc gcg ttg cta tta atg acc ttc tta ccc gag tta aag    2016
Asp Thr Asn Ile Ala Leu Leu Leu Met Thr Phe Leu Pro Glu Leu Lys
            180                 185                 190 gaa tca ttc cac gag aaa ttc ggt gac tct aaa gct ctt cag ctg tca    2064
Glu Ser Phe His Glu Lys Phe Gly Asp Ser Lys Ala Leu Gln Leu Ser
        195                 200                 205 caa gtc att aga ttc tgt aaa tta aag gcg tca tcg aat tca tta tct    2112
Gln Val Ile Arg Phe Cys Lys Leu Lys Ala Ser Ser Asn Ser Leu Ser
    210                 215                 220 tca gtc tca gat gca ttg gtt gca caa gac aga aga agc tat caa aag    2160
Ser Val Ser Asp Ala Leu Val Ala Gln Asp Arg Arg Ser Tyr Gln Lys
225                 230                 235                 240 aaa gga aat aag gga tgt atg att tgt ggg gct gat cat cgc tta agc    2208
Lys Gly Asn Lys Gly Cys Met Ile Cys Gly Ala Asp His Arg Leu Ser
            245                 250                 255 aac tgt tct ctg ctt aaa aga aga ata cca gaa gcc aga atc ttt aaa    2256
Asn Cys Ser Leu Leu Lys Arg Arg Ile Pro Glu Ala Arg Ile Phe Lys
            260                 265                 270 tta tat cct aat gac aag acg aat aga tct tca tct gct agt gtt gcg    2304
Leu Tyr Pro Asn Asp Lys Thr Asn Arg Ser Ser Ser Ala Ser Val Ala
        275                 280                 285 att cct gac tat gaa acg caa ggc caa aca gca gga cag ata aca cca    2352
Ile Pro Asp Tyr Glu Thr Gln Gly Gln Thr Ala Gly Gln Ile Thr Pro
    290                 295                 300 aag tcc tgg ctc tgt atg tta tct tcg acc gtc cca gct acc aaa tcc    2400
Lys Ser Trp Leu Cys Met Leu Ser Ser Thr Val Pro Ala Thr Lys Ser
305                 310                 315                 320 tca gat tgg att tgt gac aca gga tgt act tca cac atg tgc cac gac    2448
Ser Asp Trp Ile Cys Asp Thr Gly Cys Thr Ser His Met Cys His Asp
            325                 330                 335 cgt tct atg ttc tca tca ttt act aga tcc tct aag aaa gac ttt gtc    2496
Arg Ser Met Phe Ser Ser Phe Thr Arg Ser Ser Lys Lys Asp Phe Val
            340                 345                 350 aga gga gtc ggc ggt tcc ata ccc atc atg ggc tcc ggg act gta aac    2544
Arg Gly Val Gly Gly Ser Ile Pro Ile Met Gly Ser Gly Thr Val Asn
        355                 360                 365 atc ggc act gtt caa tta aat gac gta tcc tac gtc cct gat tta cca    2592
Ile Gly Thr Val Gln Leu Asn Asp Val Ser Tyr Val Pro Asp Leu Pro
    370                 375                 380 gtc aac cta ata tcc att tgg aaa cta tgt gct aaa tcc aac tct tct    2640
Val Asn Leu Ile Ser Ile Trp Lys Leu Cys Ala Lys Ser Asn Ser Ser
385                 390                 395                 400 gtt acg ttc aca aaa gag ggt gtc act gtg aaa tca cct gat gac gtg    2688
Val Thr Phe Thr Lys Glu Gly Val Thr Val Lys Ser Pro Asp Asp Val
            405                 410                 415 att tct acg gct ggg aag tta aac aat tat ctg tac att ttc gat gat    2736
Ile Ser Thr Ala Gly Lys Leu Asn Asn Tyr Leu Tyr Ile Phe Asp Asp
            420                 425                 430 ctt acg ccc gta act acc ttc tct tcg caa aat tac ttc tgc tct aaa    2784
Leu Thr Pro Val Thr Thr Phe Ser Ser Gln Asn Tyr Phe Cys Ser Lys
        435                 440                 445 aca ttg gat tca tct aaa atg ata act tcc gca gcg ttt cat acc gtt    2832
Thr Leu Asp Ser Ser Lys Met Ile Thr Ser Ala Ala Phe His Thr Val
    450                 455                 460 gca gat aaa atg ttg tcg caa cac att tct ccc act gct ctc ccg gta    2880
Ala Asp Lys Met Leu Ser Gln His Ile Ser Pro Thr Ala Leu Pro Val
```

```
                     -continued
465              470              475              480 aaa tgg cat gct cgt atg ggc cat ccc gga gca gat att tac aat tcc   2928
Lys Trp His Ala Arg Met Gly His Pro Gly Ala Asp Ile Tyr Asn Ser
                485              490              495 ttg gct aga act ctg cgt ttt cca aaa ttt aag acg gct gaa tac act   2976
Leu Ala Arg Thr Leu Arg Phe Pro Lys Phe Lys Thr Ala Glu Tyr Thr
            500              505              510 att tgt cct acc tgc tca cta gca aaa gga atc atc aaa aag ggt aaa   3024
Ile Cys Pro Thr Cys Ser Leu Ala Lys Gly Ile Ile Lys Lys Gly Lys
        515              520              525 gtc tcg ctc aaa aaa tat acc caa cct ctt caa atg gta cag gct gat   3072
Val Ser Leu Lys Lys Tyr Thr Gln Pro Leu Gln Met Val Gln Ala Asp
    530              535              540 ctc tgt ggt ggg ttt cgc tac caa gag ttt cag tca aat aaa tat ttt   3120
Leu Cys Gly Gly Phe Arg Tyr Gln Glu Phe Gln Ser Asn Lys Tyr Phe
545              550              555              560 ctt act atc cgt gat gcc tat agt cgc tac tac tct gta ata cat tta   3168
Leu Thr Ile Arg Asp Ala Tyr Ser Arg Tyr Tyr Ser Val Ile His Leu
                565              570              575 aaa tcc aaa gca gac gct ccg ata aaa ttc atg gaa tgg atc aac gaa   3216
Lys Ser Lys Ala Asp Ala Pro Ile Lys Phe Met Glu Trp Ile Asn Glu
            580              585              590 acc gaa caa tac ttt agc tcc cgg ggt gga ttc aaa gtc gga tct gtt   3264
Thr Glu Gln Tyr Phe Ser Ser Arg Gly Gly Phe Lys Val Gly Ser Val
        595              600              605 cgt aca gac aat ggt aca gaa ttc gta aat aaa aat ctt cat gcg ttt   3312
Arg Thr Asp Asn Gly Thr Glu Phe Val Asn Lys Asn Leu His Ala Phe
    610              615              620 ttt aaa tct aaa gga ata gag cat cag tta act att cca tat cat agt   3360
Phe Lys Ser Lys Gly Ile Glu His Gln Leu Thr Ile Pro Tyr His Ser
625              630              635              640 tat caa aat ggt gct gtt gaa cgt gca cat cgt acc atc gaa gaa cgc   3408
Tyr Gln Asn Gly Ala Val Glu Arg Ala His Arg Thr Ile Glu Glu Arg
                645              650              655 act cgt tgt ctc ctt atc ggg ggg cgt gtt cct ccg tcc ttg tgg tct   3456
Thr Arg Cys Leu Leu Ile Gly Gly Arg Val Pro Pro Ser Leu Trp Ser
            660              665              670 gaa gct gtt tct tgc gca gtc tat tta atc aat agg tcc cct gta gtg   3504
Glu Ala Val Ser Cys Ala Val Tyr Leu Ile Asn Arg Ser Pro Val Val
        675              680              685 tcc aaa aat aac agt atc cca tac tgc cgg tgg ttc aac atc ccc gca   3552
Ser Lys Asn Asn Ser Ile Pro Tyr Cys Arg Trp Phe Asn Ile Pro Ala
    690              695              700 aaa gat ttc ggt atc gca cat ctt cga att ttt gga tgt aca gca tac   3600
Lys Asp Phe Gly Ile Ala His Leu Arg Ile Phe Gly Cys Thr Ala Tyr
705              710              715              720 gca acc tta caa cct agt ctt cga gac ggc aaa ctt gcc cca act gtc   3648
Ala Thr Leu Gln Pro Ser Leu Arg Asp Gly Lys Leu Ala Pro Thr Val
                725              730              735 ata tct ggt gtt atg gtt ggc tat gac tct aac cat cga gga tac agg   3696
Ile Ser Gly Val Met Val Gly Tyr Asp Ser Asn His Arg Gly Tyr Arg
            740              745              750 att tat cat ccc gaa act ggc cgc atc ttt gtg agc agt caa gtt cga   3744
Ile Tyr His Pro Glu Thr Gly Arg Ile Phe Val Ser Ser Gln Val Arg
        755              760              765 ttt gac gaa cac atg ttt cct ctt gct gat aca gag gca gtt cac gtc   3792
Phe Asp Glu His Met Phe Pro Leu Ala Asp Thr Glu Ala Val His Val
    770              775              780 tct cac gac ttt gcc act tcc gct att ggg ggg gtg tcc aaa tat cct   3840
```

-continued

```
                Ser His Asp Phe Ala Thr Ser Ala Ile Gly Gly Val Ser Lys Tyr Pro
                785                 790                 795                 800 gaa aca ggg tca acc gtc tct gct cca aag aac gac gga tct gac ttg           3888
Glu Thr Gly Ser Thr Val Ser Ala Pro Lys Asn Asp Gly Ser Asp Leu
                    805                 810                 815 gca aat ttg cca ata act gtt ccc aaa aat gta aat caa cca gca cat           3936
Ala Asn Leu Pro Ile Thr Val Pro Lys Asn Val Asn Gln Pro Ala His
                820                 825                 830 aaa cct aat acc agt aac atc tct tcc tct gat gat gat gag gat att           3984
Lys Pro Asn Thr Ser Asn Ile Ser Ser Ser Asp Asp Asp Glu Asp Ile
            835                 840                 845 tca atg gaa atc gaa atg gaa aaa cct atc cct gag tgt aac caa gac           4032
Ser Met Glu Ile Glu Met Glu Lys Pro Ile Pro Glu Cys Asn Gln Asp
        850                 855                 860 aac tta cca aac tcc gga tgt cca cca aca agg ata caa cat tct aac           4080
Asn Leu Pro Asn Ser Gly Cys Pro Pro Thr Arg Ile Gln His Ser Asn
865                 870                 875                 880 ttt gaa tcc tta cca acc gtg tct acc gaa gac gaa act aat tct tct           4128
Phe Glu Ser Leu Pro Thr Val Ser Thr Glu Asp Glu Thr Asn Ser Ser
                    885                 890                 895 atg gag aaa act cct gaa aga gtt cca gcg gca cta act tat cga gaa           4176
Met Glu Lys Thr Pro Glu Arg Val Pro Ala Ala Leu Thr Tyr Arg Glu
                900                 905                 910 att cca aaa tca tcc gat tca gaa tat att ccg aca tgc cga aat aga           4224
Ile Pro Lys Ser Ser Asp Ser Glu Tyr Ile Pro Thr Cys Arg Asn Arg
            915                 920                 925 act aga cgt gtt aaa aga act aat aag aaa cca acg cga tcc cgc gaa           4272
Thr Arg Arg Val Lys Arg Thr Asn Lys Lys Pro Thr Arg Ser Arg Glu
        930                 935                 940 ata gaa ata tat gat ata tca cgt cca aac gta ata tcg agt gac aac           4320
Ile Glu Ile Tyr Asp Ile Ser Arg Pro Asn Val Ile Ser Ser Asp Asn
945                 950                 955                 960 tta cct gaa gtt aga agt gcc aag caa aga aag acg gtg tcc aat aca           4368
Leu Pro Glu Val Arg Ser Ala Lys Gln Arg Lys Thr Val Ser Asn Thr
                    965                 970                 975 aat gat act gta gca agg aca aat aga ctt cca acc gtg cta cga act           4416
Asn Asp Thr Val Ala Arg Thr Asn Arg Leu Pro Thr Val Leu Arg Thr
                980                 985                 990 cta gac tca aac aac att gac acg ctg cat gtt gcc agt act ggt gaa           4464
Leu Asp Ser Asn Asn Ile Asp Thr Leu His Val Ala Ser Thr Gly Glu
            995                 1000                1005 gaa gtg tcc atc gaa aga ctt tca agc atg gct ctt cag gaa gcg aag           4512
Glu Val Ser Ile Glu Arg Leu Ser Ser Met Ala Leu Gln Glu Ala Lys
        1010                1015                1020 aac aat tcc gcc aga act aat caa gct aat tct ctt act gat tgg ttt           4560
Asn Asn Ser Ala Arg Thr Asn Gln Ala Asn Ser Leu Thr Asp Trp Phe
1025                1030                1035                1040 cca gta ggc gca atg ccg ata cct gac cag agg tat cta tcc gtt cac           4608
Pro Val Gly Ala Met Pro Ile Pro Asp Gln Arg Tyr Leu Ser Val His
                    1045                1050                1055 gat gga aca tat atc agc gac tca caa gat gtg ggt gat act gac ctc           4656
Asp Gly Thr Tyr Ile Ser Asp Ser Gln Asp Val Gly Asp Thr Asp Leu
                1060                1065                1070 act cct gct gta acc agg cta gtt act gaa gag aat tca atc gaa tct           4704
Thr Pro Ala Val Thr Arg Leu Val Thr Glu Glu Asn Ser Ile Glu Ser
            1075                1080                1085 cct cca tcg ttg gat tca tcg cct cca aat acc tca ttt aac gcg gct           4752
Pro Pro Ser Leu Asp Ser Ser Pro Pro Asn Thr Ser Phe Asn Ala Ala
        1090                1095                1100
```

-continued

```
cta act gct att atc cat agc aca aaa aaa gga aac ccg aaa acc tat        4800
Leu Thr Ala Ile Ile His Ser Thr Lys Lys Gly Asn Pro Lys Thr Tyr
1105                1110                1115                1120 gcc caa gca atg gga agg cct gac ttt caa gaa tgg cac aac gca tgc        4848
Ala Gln Ala Met Gly Arg Pro Asp Phe Gln Glu Trp His Asn Ala Cys
            1125                1130                1135 ctc aag gaa ctt tcc gcg ttc aaa gat cac aat acg tac aaa ttg gtg        4896
Leu Lys Glu Leu Ser Ala Phe Lys Asp His Asn Thr Tyr Lys Leu Val
        1140                1145                1150 tct ctt cca aag caa aga aga gct ctt gga tcg cgc tgg gta ttc aca        4944
Ser Leu Pro Lys Gln Arg Arg Ala Leu Gly Ser Arg Trp Val Phe Thr
    1155                1160                1165 ata aaa gac tcc ggg acg tac aaa gct cgc ctt gtc gcc caa gga cat        4992
Ile Lys Asp Ser Gly Thr Tyr Lys Ala Arg Leu Val Ala Gln Gly His
1170                1175                1180 act caa aag gct ggt att gac tat caa gaa act ttt gca cca gtc att        5040
Thr Gln Lys Ala Gly Ile Asp Tyr Gln Glu Thr Phe Ala Pro Val Ile
1185                1190                1195                1200 cga tat gac tct gtt aga tta ttt ctg gcc ctt gct agc tgc ctc aaa        5088
Arg Tyr Asp Ser Val Arg Leu Phe Leu Ala Leu Ala Ser Cys Leu Lys
            1205                1210                1215 cta ata gta tat cag atg gac gtt gac acc gcg ttt cta aac tca aaa        5136
Leu Ile Val Tyr Gln Met Asp Val Asp Thr Ala Phe Leu Asn Ser Lys
        1220                1225                1230 atg aat gag ccg gta tac gta aaa caa cca ccc gga ttt att aat gaa        5184
Met Asn Glu Pro Val Tyr Val Lys Gln Pro Pro Gly Phe Ile Asn Glu
    1235                1240                1245 agt aat ccc gac tat gta tgg gaa cta tac ggc ggt atg tat gga ctc        5232
Ser Asn Pro Asp Tyr Val Trp Glu Leu Tyr Gly Gly Met Tyr Gly Leu
1250                1255                1260 aag caa gcc cca tta cta tgg aac gaa cat atc aac aat act ctt caa        5280
Lys Gln Ala Pro Leu Leu Trp Asn Glu His Ile Asn Asn Thr Leu Gln
1265                1270                1275                1280 aag att ggt ttt cgt cga cat gaa ggc gaa cat ggc tta tac ttt cgt        5328
Lys Ile Gly Phe Arg Arg His Glu Gly Glu His Gly Leu Tyr Phe Arg
            1285                1290                1295 tcc aca tct gat ggt ccc atc tac att gcc cta tac gta gac gac tta        5376
Ser Thr Ser Asp Gly Pro Ile Tyr Ile Ala Leu Tyr Val Asp Asp Leu
        1300                1305                1310 ctt gtt gct gct ccc tct ccg aaa ata tat gac agg gtt aag cag aaa        5424
Leu Val Ala Ala Pro Ser Pro Lys Ile Tyr Asp Arg Val Lys Gln Lys
    1315                1320                1325 cta acg aag tta tac tca atg aag gat cta ggt aaa gtt gac aaa ttc        5472
Leu Thr Lys Leu Tyr Ser Met Lys Asp Leu Gly Lys Val Asp Lys Phe
1330                1335                1340 ctc ggt ctt aac att aat caa ttt tca aat gga gac atc act ctc tca        5520
Leu Gly Leu Asn Ile Asn Gln Phe Ser Asn Gly Asp Ile Thr Leu Ser
1345                1350                1355                1360 ctt caa gac tat att gct aaa gct gca tct gaa agc gaa ata aac ata        5568
Leu Gln Asp Tyr Ile Ala Lys Ala Ala Ser Glu Ser Glu Ile Asn Ile
            1365                1370                1375 tgt aag cct aca cag act ccg ctc tgt gac tca aag cct ctt ttc gaa        5616
Cys Lys Pro Thr Gln Thr Pro Leu Cys Asp Ser Lys Pro Leu Phe Glu
        1380                1385                1390 aca act tcc ccg cac cta aag gac atc act cct tat cag agc ata gtt        5664
Thr Thr Ser Pro His Leu Lys Asp Ile Thr Pro Tyr Gln Ser Ile Val
    1395                1400                1405 gga cag ctt ctc ttt tgt gca aat act ggt cgt cct gac ata tct tat        5712
Gly Gln Leu Leu Phe Cys Ala Asn Thr Gly Arg Pro Asp Ile Ser Tyr
1410                1415                1420
```

```
ccg gtc tca cta ctc tcc agg ttt ctt cgc gaa cct cgc gca atc cat    5760
Pro Val Ser Leu Leu Ser Arg Phe Leu Arg Glu Pro Arg Ala Ile His
1425                1430                1435                1440 ttg gag tct gct cga cga gtt cta cgg tac cta tat acc acc aga agt    5808
Leu Glu Ser Ala Arg Arg Val Leu Arg Tyr Leu Tyr Thr Thr Arg Ser
            1445                1450                1455 atg tgt ctc aag tat cgt tct gga tct ctg ttg gca cta act gta tat    5856
Met Cys Leu Lys Tyr Arg Ser Gly Ser Leu Leu Ala Leu Thr Val Tyr
        1460                1465                1470 tgt gat gca tct cat gga gca att cac gat ctc cca cac tct act ggg    5904
Cys Asp Ala Ser His Gly Ala Ile His Asp Leu Pro His Ser Thr Gly
    1475                1480                1485 ggg tac gtg act cta ctt gct ggt gct cca gtt acg tgg tca tca aag    5952
Gly Tyr Val Thr Leu Leu Ala Gly Ala Pro Val Thr Trp Ser Ser Lys
1490                1495                1500 aaa ctc aag ggt gtg att cct gta tca tct act gag gca gaa tac att    6000
Lys Leu Lys Gly Val Ile Pro Val Ser Ser Thr Glu Ala Glu Tyr Ile
1505                1510                1515                1520 act gca agt gaa act gtc atg gag ata gaa tgg att caa aac ttg ttt    6048
Thr Ala Ser Glu Thr Val Met Glu Ile Glu Trp Ile Gln Asn Leu Phe
                1525                1530                1535 gaa cac tta ggc cag cca ctt atc tca tca aca tta tac gta gat aat    6096
Glu His Leu Gly Gln Pro Leu Ile Ser Ser Thr Leu Tyr Val Asp Asn
            1540                1545                1550 gaa cct gct ata aaa cta tct aaa cat cct gta ttt cac acg aga aca    6144
Glu Pro Ala Ile Lys Leu Ser Lys His Pro Val Phe His Thr Arg Thr
        1555                1560                1565 aaa cac att gcc ttg aga tat cac aag cta aga agt gca gtg gca gca    6192
Lys His Ile Ala Leu Arg Tyr His Lys Leu Arg Ser Ala Val Ala Ala
    1570                1575                1580 ggc ata att acc ata gag cat gtt att aca aag aga caa gtt gct gac    6240
Gly Ile Ile Thr Ile Glu His Val Ile Thr Lys Arg Gln Val Ala Asp
1585                1590                1595                1600 ata ttt aca aaa atc ctt cca gca gaa tca ttc aaa gca cat agg gct    6288
Ile Phe Thr Lys Ile Leu Pro Ala Glu Ser Phe Lys Ala His Arg Ala
                1605                1610                1615 gtc atg gtg agg gaa cca gaa act gca aaa taaccactct catgcgtatt     6338
Val Met Val Arg Glu Pro Glu Thr Ala Lys
            1620                1625 cagttatggg gggatgttga atgtgataac ccaaaagcat gatatgggta atgtttcagt  6398
actgtttcag aattgtttca gtaatgtttt agacaaggaa aacatagagc agcaaacctc  6458
cgatccgaca gtacttaaga aaccatagtt tctgtgtaca agagtagtac ctatgtaatt  6518
cttacattta cataacatat agaaaggtcc aataaactta caacattatg acatataagc  6578
tagatcgtaa ttcactacgt caacatcgta cacttaaaat atatgtatgt atctgcacta  6638
tttagtcttg ttttattggg tg                                          6660

<210> SEQ ID NO 2
<211> LENGTH: 1626
<212> TYPE: PRT
<213> ORGANISM: Saccharomyces paradoxus

<400> SEQUENCE: 2

Met Thr Tyr Lys Leu Asp Arg Asn Ser Leu Arg Gln Gln Val Met Ser
 1               5                  10                  15

Pro Glu Ser Asn Ala Ser Glu Thr Ile Ile Asn Leu Ser Asn Pro Asn
            20                  25                  30
```

-continued

```
Asn Tyr Lys Gln Trp Leu Tyr Gly Ile Glu Thr Ala Ala Glu Tyr Ala
         35                  40                  45
Asn Glu Tyr Met Asn Glu Phe Val His Thr Gly Asp Ile Gln Ser Met
     50                  55                  60
Lys Arg Asp Tyr Asn Leu Ser Ala Asn Asp Glu Ser Phe Val Lys Thr
 65                  70                  75                  80
Val Phe Asn Ser Phe Leu Val Lys Leu Tyr Lys Lys Thr Ile Val Gly
                 85                  90                  95
Glu Ala Ala Cys Glu Met Asn Trp Ile Cys Asp Asp Ser Leu Gly Arg
                100                 105                 110
Val Ser Ala Tyr Asp Ile Phe Ser His Phe Glu Glu Asn Tyr Asn Glu
             115                 120                 125
Val Thr Ile Gly Ser Arg Leu Thr Leu Ile Glu Asp Leu Pro Asn Ile
         130                 135                 140
Ser Ser Lys Pro Val Asp Glu Ile Ala Ser Phe Leu Lys Thr Leu Phe
145                 150                 155                 160
Thr Met Leu Glu Asp Asn Ser Glu Glu Gln Asp Lys Lys Arg Arg
                165                 170                 175
Asp Thr Asn Ile Ala Leu Leu Leu Met Thr Phe Leu Pro Glu Leu Lys
                180                 185                 190
Glu Ser Phe His Glu Lys Phe Gly Asp Ser Lys Ala Leu Gln Leu Ser
            195                 200                 205
Gln Val Ile Arg Phe Cys Lys Leu Lys Ala Ser Ser Asn Ser Leu Ser
        210                 215                 220
Ser Val Ser Asp Ala Leu Val Ala Gln Asp Arg Arg Ser Tyr Gln Lys
225                 230                 235                 240
Lys Gly Asn Lys Gly Cys Met Ile Cys Gly Ala Asp His Arg Leu Ser
                245                 250                 255
Asn Cys Ser Leu Leu Lys Arg Arg Ile Pro Glu Ala Arg Ile Phe Lys
            260                 265                 270
Leu Tyr Pro Asn Asp Lys Thr Asn Arg Ser Ser Ser Ala Ser Val Ala
        275                 280                 285
Ile Pro Asp Tyr Glu Thr Gln Gly Gln Thr Ala Gly Gln Ile Thr Pro
    290                 295                 300
Lys Ser Trp Leu Cys Met Leu Ser Ser Thr Val Pro Ala Thr Lys Ser
305                 310                 315                 320
Ser Asp Trp Ile Cys Asp Thr Gly Cys Thr Ser His Met Cys His Asp
                325                 330                 335
Arg Ser Met Phe Ser Ser Phe Thr Arg Ser Ser Lys Lys Asp Phe Val
            340                 345                 350
Arg Gly Val Gly Gly Ser Ile Pro Ile Met Gly Ser Gly Thr Val Asn
        355                 360                 365
Ile Gly Thr Val Gln Leu Asn Asp Val Ser Tyr Val Pro Asp Leu Pro
    370                 375                 380
Val Asn Leu Ile Ser Ile Trp Lys Leu Cys Ala Lys Ser Asn Ser Ser
385                 390                 395                 400
Val Thr Phe Thr Lys Glu Gly Val Thr Val Lys Ser Pro Asp Val
                405                 410                 415
Ile Ser Thr Ala Gly Lys Leu Asn Asn Tyr Leu Tyr Ile Phe Asp Asp
            420                 425                 430
Leu Thr Pro Val Thr Thr Phe Ser Ser Gln Asn Tyr Phe Cys Ser Lys
        435                 440                 445
Thr Leu Asp Ser Ser Lys Met Ile Thr Ser Ala Ala Phe His Thr Val
```

-continued

```
          450                 455                 460
Ala Asp Lys Met Leu Ser Gln His Ile Ser Pro Thr Ala Leu Pro Val
465                 470                 475                 480
Lys Trp His Ala Arg Met Gly His Pro Gly Ala Asp Ile Tyr Asn Ser
                    485                 490                 495
Leu Ala Arg Thr Leu Arg Phe Pro Lys Phe Lys Thr Ala Glu Tyr Thr
                500                 505                 510
Ile Cys Pro Thr Cys Ser Leu Ala Lys Gly Ile Ile Lys Lys Gly Lys
                515                 520                 525
Val Ser Leu Lys Lys Tyr Thr Gln Pro Leu Gln Met Val Gln Ala Asp
530                 535                 540
Leu Cys Gly Gly Phe Arg Tyr Gln Glu Phe Gln Ser Asn Lys Tyr Phe
545                 550                 555                 560
Leu Thr Ile Arg Asp Ala Tyr Ser Arg Tyr Tyr Ser Val Ile His Leu
                565                 570                 575
Lys Ser Lys Ala Asp Ala Pro Ile Lys Phe Met Glu Trp Ile Asn Glu
                580                 585                 590
Thr Glu Gln Tyr Phe Ser Ser Arg Gly Gly Phe Lys Val Gly Ser Val
                595                 600                 605
Arg Thr Asp Asn Gly Thr Glu Phe Val Asn Lys Asn Leu His Ala Phe
610                 615                 620
Phe Lys Ser Lys Gly Ile Glu His Gln Leu Thr Ile Pro Tyr His Ser
625                 630                 635                 640
Tyr Gln Asn Gly Ala Val Glu Arg Ala His Arg Thr Ile Glu Glu Arg
                645                 650                 655
Thr Arg Cys Leu Leu Ile Gly Gly Arg Val Pro Pro Ser Leu Trp Ser
                660                 665                 670
Glu Ala Val Ser Cys Ala Val Tyr Leu Ile Asn Arg Ser Pro Val Val
                675                 680                 685
Ser Lys Asn Asn Ser Ile Pro Tyr Cys Arg Trp Phe Asn Ile Pro Ala
690                 695                 700
Lys Asp Phe Gly Ile Ala His Leu Arg Ile Phe Gly Cys Thr Ala Tyr
705                 710                 715                 720
Ala Thr Leu Gln Pro Ser Leu Arg Asp Gly Lys Leu Ala Pro Thr Val
                725                 730                 735
Ile Ser Gly Val Met Val Gly Tyr Asp Ser Asn His Arg Gly Tyr Arg
                740                 745                 750
Ile Tyr His Pro Glu Thr Gly Arg Ile Phe Val Ser Ser Gln Val Arg
                755                 760                 765
Phe Asp Glu His Met Phe Pro Leu Ala Asp Thr Glu Ala Val His Val
770                 775                 780
Ser His Asp Phe Ala Thr Ser Ala Ile Gly Gly Val Ser Lys Tyr Pro
785                 790                 795                 800
Glu Thr Gly Ser Thr Val Ser Ala Pro Lys Asn Asp Gly Ser Asp Leu
                805                 810                 815
Ala Asn Leu Pro Ile Thr Val Pro Lys Asn Val Asn Gln Pro Ala His
                820                 825                 830
Lys Pro Asn Thr Ser Asn Ile Ser Ser Ser Asp Asp Asp Glu Asp Ile
                835                 840                 845
Ser Met Glu Ile Glu Met Glu Lys Pro Ile Pro Glu Cys Asn Gln Asp
850                 855                 860
Asn Leu Pro Asn Ser Gly Cys Pro Pro Thr Arg Ile Gln His Ser Asn
865                 870                 875                 880
```

-continued

```
Phe Glu Ser Leu Pro Thr Val Ser Thr Glu Asp Glu Thr Asn Ser Ser
                885                 890                 895
Met Glu Lys Thr Pro Glu Arg Val Pro Ala Ala Leu Thr Tyr Arg Glu
            900                 905                 910
Ile Pro Lys Ser Ser Asp Ser Glu Tyr Ile Pro Thr Cys Arg Asn Arg
            915                 920                 925
Thr Arg Arg Val Lys Arg Thr Asn Lys Lys Pro Thr Arg Ser Arg Glu
        930                 935                 940
Ile Glu Ile Tyr Asp Ile Ser Arg Pro Asn Val Ile Ser Ser Asp Asn
945                 950                 955                 960
Leu Pro Glu Val Arg Ser Ala Lys Gln Arg Lys Thr Val Ser Asn Thr
                965                 970                 975
Asn Asp Thr Val Ala Arg Thr Asn Arg Leu Pro Thr Val Leu Arg Thr
            980                 985                 990
Leu Asp Ser Asn Asn Ile Asp Thr Leu His Val Ala Ser Thr Gly Glu
            995                 1000                1005
Glu Val Ser Ile Glu Arg Leu Ser Ser Met Ala Leu Gln Glu Ala Lys
        1010                1015                1020
Asn Asn Ser Ala Arg Thr Asn Gln Ala Asn Ser Leu Thr Asp Trp Phe
1025                1030                1035                1040
Pro Val Gly Ala Met Pro Ile Pro Asp Gln Arg Tyr Leu Ser Val His
                1045                1050                1055
Asp Gly Thr Tyr Ile Ser Asp Ser Gln Asp Val Gly Asp Thr Asp Leu
            1060                1065                1070
Thr Pro Ala Val Thr Arg Leu Val Thr Glu Glu Asn Ser Ile Glu Ser
            1075                1080                1085
Pro Pro Ser Leu Asp Ser Ser Pro Asn Thr Ser Phe Asn Ala Ala
        1090                1095                1100
Leu Thr Ala Ile Ile His Ser Thr Lys Lys Gly Asn Pro Lys Thr Tyr
1105                1110                1115                1120
Ala Gln Ala Met Gly Arg Pro Asp Phe Gln Glu Trp His Asn Ala Cys
                1125                1130                1135
Leu Lys Glu Leu Ser Ala Phe Lys Asp His Asn Thr Tyr Lys Leu Val
                1140                1145                1150
Ser Leu Pro Lys Gln Arg Arg Ala Leu Gly Ser Arg Trp Val Phe Thr
                1155                1160                1165
Ile Lys Asp Ser Gly Thr Tyr Lys Ala Arg Leu Val Ala Gln Gly His
            1170                1175                1180
Thr Gln Lys Ala Gly Ile Asp Tyr Gln Glu Thr Phe Ala Pro Val Ile
1185                1190                1195                1200
Arg Tyr Asp Ser Val Arg Leu Phe Leu Ala Leu Ala Ser Cys Leu Lys
            1205                1210                1215
Leu Ile Val Tyr Gln Met Asp Val Asp Thr Ala Phe Leu Asn Ser Lys
                1220                1225                1230
Met Asn Glu Pro Val Tyr Val Lys Gln Pro Pro Gly Phe Ile Asn Glu
            1235                1240                1245
Ser Asn Pro Asp Tyr Val Trp Glu Leu Tyr Gly Gly Met Tyr Gly Leu
        1250                1255                1260
Lys Gln Ala Pro Leu Leu Trp Asn Glu His Ile Asn Asn Thr Leu Gln
1265                1270                1275                1280
Lys Ile Gly Phe Arg Arg His Glu Gly Glu His Gly Leu Tyr Phe Arg
                1285                1290                1295
```

-continued

```
Ser Thr Ser Asp Gly Pro Ile Tyr Ile Ala Leu Tyr Val Asp Asp Leu
            1300                1305                1310

Leu Val Ala Ala Pro Ser Pro Lys Ile Tyr Asp Arg Val Lys Gln Lys
        1315                1320                1325

Leu Thr Lys Leu Tyr Ser Met Lys Asp Leu Gly Lys Val Asp Lys Phe
    1330                1335                1340

Leu Gly Leu Asn Ile Asn Gln Phe Ser Asn Gly Asp Ile Thr Leu Ser
1345                1350                1355                1360

Leu Gln Asp Tyr Ile Ala Lys Ala Ala Ser Glu Ser Glu Ile Asn Ile
            1365                1370                1375

Cys Lys Pro Thr Gln Thr Pro Leu Cys Asp Ser Lys Pro Leu Phe Glu
        1380                1385                1390

Thr Thr Ser Pro His Leu Lys Asp Ile Thr Pro Tyr Gln Ser Ile Val
    1395                1400                1405

Gly Gln Leu Leu Phe Cys Ala Asn Thr Gly Arg Pro Asp Ile Ser Tyr
1410                1415                1420

Pro Val Ser Leu Leu Ser Arg Phe Leu Arg Glu Pro Arg Ala Ile His
1425                1430                1435                1440

Leu Glu Ser Ala Arg Arg Val Leu Arg Tyr Leu Tyr Thr Thr Arg Ser
            1445                1450                1455

Met Cys Leu Lys Tyr Arg Ser Gly Ser Leu Leu Ala Leu Thr Val Tyr
        1460                1465                1470

Cys Asp Ala Ser His Gly Ala Ile His Asp Leu Pro His Ser Thr Gly
    1475                1480                1485

Gly Tyr Val Thr Leu Leu Ala Gly Ala Pro Val Thr Trp Ser Ser Lys
1490                1495                1500

Lys Leu Lys Gly Val Ile Pro Val Ser Ser Thr Glu Ala Glu Tyr Ile
1505                1510                1515                1520

Thr Ala Ser Glu Thr Val Met Glu Ile Glu Trp Ile Gln Asn Leu Phe
            1525                1530                1535

Glu His Leu Gly Gln Pro Leu Ile Ser Ser Thr Leu Tyr Val Asp Asn
        1540                1545                1550

Glu Pro Ala Ile Lys Leu Ser Lys His Pro Val Phe His Thr Arg Thr
    1555                1560                1565

Lys His Ile Ala Leu Arg Tyr His Lys Leu Arg Ser Ala Val Ala Ala
1570                1575                1580

Gly Ile Ile Thr Ile Glu His Val Ile Thr Lys Arg Gln Val Ala Asp
1585                1590                1595                1600

Ile Phe Thr Lys Ile Leu Pro Ala Glu Ser Phe Lys Ala His Arg Ala
            1605                1610                1615

Val Met Val Arg Glu Pro Glu Thr Ala Lys
            1620                1625

<210> SEQ ID NO 3
<211> LENGTH: 6
<212> TYPE: PRT
<213> ORGANISM: Saccharomyces cerevisiae

<400> SEQUENCE: 3

Leu Asp Ser Ser Pro Pro
  1               5

<210> SEQ ID NO 4
<211> LENGTH: 176
<212> TYPE: PRT
<213> ORGANISM: Saccharomyces paradoxus
```

-continued

<400> SEQUENCE: 4

Thr Thr Ile Asn Ser Lys Lys Arg Ser Leu Glu Asp Asn Glu Thr Glu
1               5                   10                  15

Ile Lys Val Ser Arg Asp Thr Trp Asn Thr Lys Asn Met Arg Ser Leu
            20                  25                  30

Glu Pro Pro Arg Ser Lys Lys Arg Ile His Leu Ile Ala Ala Val Lys
        35                  40                  45

Ala Val Lys Ser Ile Lys Pro Ile Arg Thr Thr Leu Arg Tyr Asp Glu
    50                  55                  60

Ala Ile Thr Tyr Asn Lys Asp Ile Lys Glu Lys Glu Lys Tyr Ile Glu
65                  70                  75                  80

Ala Tyr His Lys Glu Val Asn Gln Leu Leu Lys Met Lys Thr Trp Asp
                85                  90                  95

Thr Asp Glu Tyr Tyr Asp Arg Lys Glu Ile Asp Pro Lys Arg Val Ile
            100                 105                 110

Asn Ser Met Phe Ile Phe Asn Lys Lys Arg Asp Gly Thr Lys Ala Arg
        115                 120                 125

Phe Val Ala Arg Gly Asp Ile Gln His Pro Asp Thr Tyr Asp Ser Gly
    130                 135                 140

Met Gln Ser Asn Thr Val His His Tyr Ala Leu Met Thr Ser Leu Ser
145                 150                 155                 160

Leu Ala Leu Asp Asn Asn Tyr Tyr Ile Thr Gln Leu Asp Ile Ser Ser
                165                 170                 175

<210> SEQ ID NO 5
<211> LENGTH: 178
<212> TYPE: PRT
<213> ORGANISM: Saccharomyces cerevisiae

<400> SEQUENCE: 5

Thr Thr Thr Lys Ser Lys Lys Arg Ser Leu Glu Asp Asn Glu Thr Glu
1               5                   10                  15

Ile Glu Val Ser Arg Asp Thr Trp Asn Lys Asn Met Arg Ser Leu
            20                  25                  30

Glu Pro Pro Arg Ser Lys Lys Arg Ile Asn Leu Ile Ala Ala Ile Lys
        35                  40                  45

Lys Gly Val Lys Ser Ile Lys Pro Val Arg Thr Thr Leu Arg Tyr Asp
    50                  55                  60

Glu Ala Ile Thr Tyr Asn Lys Asp Asn Lys Glu Lys Asp Arg Tyr Val
65                  70                  75                  80

Glu Ala Tyr His Lys Glu Ile Ser Gln Leu Leu Lys Met Asn Thr Trp
                85                  90                  95

Asp Thr Asn Lys Tyr Tyr Asp Arg Asn Asp Ile Asp Pro Lys Lys Val
            100                 105                 110

Ile Asn Ser Met Phe Ile Phe Asn Lys Lys Arg Asp Gly Thr His Lys
        115                 120                 125

Ala Arg Phe Val Ala Arg Gly Asp Ile Gln His Pro Asp Thr Tyr Asp
    130                 135                 140

Ser Asp Met Gln Ser Asn Thr Val His His Tyr Ala Leu Met Thr Ser
145                 150                 155                 160

Leu Ser Ile Ala Leu Asp Asn Asp Tyr Tyr Ile Thr Gln Leu Asp Ile
                165                 170                 175

Ser Ser

```
<210> SEQ ID NO 6
<211> LENGTH: 176
<212> TYPE: PRT
<213> ORGANISM: Saccharomyces cerevisiae

<400> SEQUENCE: 6

Ala Phe Leu Asn Lys Glu Phe Ser Ser Leu Asn Met Lys Arg Lys Arg
 1               5                  10                  15

Lys Arg His Asp Lys Asn Asn Ser Leu Thr Ser Tyr Glu Leu Glu Arg
            20                  25                  30

Asp Lys Lys Arg Ser Lys Lys Asn Arg Val Lys Leu Ile Pro Asp Asn
        35                  40                  45

Met Glu Thr Val Ser Ala Pro Lys Ile Arg Ala Ile Tyr Tyr Asn Glu
    50                  55                  60

Ala Ile Ser Lys Asn Pro Asp Leu Lys Glu Lys His Glu Tyr Lys Gln
65                  70                  75                  80

Ala Tyr His Lys Glu Leu Gln Asn Leu Lys Asp Met Lys Val Phe Asp
                85                  90                  95

Val Asp Val Lys Tyr Ser Arg Ser Glu Ile Pro Asp Asn Leu Ile Val
            100                 105                 110

Pro Thr Asn Thr Ile Phe Thr Lys Lys Arg Asn Gly Ile Tyr Lys Ala
        115                 120                 125

Arg Ile Val Cys Arg Gly Asp Thr Gln Ser Pro Asp Thr Tyr Ser Val
    130                 135                 140

Ile Thr Thr Glu Ser Leu Asn His Asn His Ile Lys Ile Phe Leu Met
145                 150                 155                 160

Ile Ala Asn Asn Arg Asn Met Phe Met Lys Thr Leu Asp Ile Asn His
                165                 170                 175

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 7

Ser Pro Pro Ser Ser Asp Ser Ser Pro Pro Asn Thr Ser
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 8

Ser Pro Pro Ser Leu Asp Ser Ser Pro Leu Asn Thr Ser
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 9
```

```
Ser Pro Pro Ser Leu Asp Ser Ser Pro Gln Asn Thr Ser
 1               5                  10
```

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 10

```
Ser Pro Pro Ser Leu Asp Ser Leu Pro Pro Asn Thr Ser
 1               5                  10
```

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 11

```
Ser Pro Pro Ser Leu Asp Pro Ser Pro Pro Asn Thr Ser
 1               5                  10
```

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 12

```
Ser Pro Pro Ser Leu Asp Ser Pro Pro Pro Asn Thr Ser
 1               5                  10
```

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 13

```
Ser Pro Pro Ser Val Asp Ser Pro Pro Pro Asn Thr Ser
 1               5                  10
```

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 14

```
Ala Pro Pro Ala Leu Asp Ser Ser Pro Pro Asn Thr Ser
 1               5                  10
```

<210> SEQ ID NO 15
<211> LENGTH: 13
<212> TYPE: PRT
<213> ORGANISM: Artificial Sequence

```
<220> FEATURE:
<223> OTHER INFORMATION: Description of Artificial Sequence:mxutant
      peptide sequence

<400> SEQUENCE: 15

Ser Ala Pro Ser Leu Asp Ser Ser Pro Pro Asn Thr Ser
 1               5                  10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 16

Ser Pro Ala Ser Leu Asp Ser Ser Pro Pro Asn Thr Ser
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 17

Ser Ala Ala Ser Leu Asp Ser Ser Pro Pro Asn Thr Ser
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 18

Ser Pro Pro Ser Leu Asp Ser Ser Pro Pro Asn Ala Ala
 1               5                  10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 19

Ser Pro Pro Ser Leu Asp Ser Ser Pro Pro Ala Thr Ser
 1               5                  10

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 20

Ser Asp Ser Ser Pro Pro
 1               5
```

```
<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 21

Leu Asp Ser Ser Pro Leu
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 22

Leu Asp Ser Ser Pro Gln
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 23

Leu Asp Ser Leu Pro Pro
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 24

Leu Asp Pro Ser Pro Pro
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence:mxutant
      peptide sequence

<400> SEQUENCE: 25

Leu Asp Ser Pro Pro Pro
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:mxutant
      peptide sequence
```

```
-continued

<400> SEQUENCE: 26

Val Asp Ser Pro Pro Pro
 1               5
```

We claim:

1. A method for targeting integration of a retrotransposon of the Ty1-copia group to a desired location on a chromosome, said method comprising the steps of;

(a) modifying an integrase in a retrotransposon so that said integrase contains a coding sequence for a peptide portion which specifically binds to a protein bound to a chromosome or which specifically binds to a particular nucleic acid sequence on a chromosome to produce a modified retrotransposon;

(b) incorporating the modified retrotransposon into a vector which is introduced into a cell comprising the chromosome with the desired location into which targeted integration is desired; and (c) introducing the vector into a cell, whereby integration of the modified retrotransposon to a desired location on a chromosome is accomplished.

2. The method of claim 1 wherein said modified retrotransposon has an integrase encoding a peptide portion which specifically binds to a protein which specifically binds to a desired location on a chromosome.

3. The method of claim 1 wherein said peptide portion specifically binds to a particular nucleic acid sequence on a chromosome.

4. The method of claim 1 wherein a targeting portion of an integrase of said retrotransposon is replaced by a peptide portion which specifically binds to a protein bound to a chromosome or which specifically binds to a particular nucleic acid sequence on a chromosome.

5. The method of claim 1 wherein the desired location on a chromosome is silent chromatin.

6. The method of claim 1 wherein said cell is a yeast cell.

7. The method of claim 1 wherein said retrotransposon is selected from the group consisting of copia, Tnt1, Ty1, Ty2, Ty4, and Ty5.

8. The method of claim 2 wherein said peptide portion is taken from the amino acid sequence of a protein which specifically binds to a transcription factor.

9. The method of claim 5 wherein the peptide portion has an amino acid sequence as given in SEQ ID NO:3.

10. The method of claim 9 wherein said cell is a yeast cell.

11. A modified Ty5 retrotransposon having an integrase which directs integration of the modified Ty5 retrotransposon more randomly within chromatin than does Ty5 having an integrase amino acid sequence as given in SEQ ID NO:2.

12. The modified Ty5 retrotransposon of claim 11 wherein the integrase has an amino acid sequence which varies at least one position of amino acids 1092–1097 from the amino acid sequence as given in SEQ ID NO:2.

13. The modified Ty5 retrotransposon of claim 11 wherein the amino acid sequence varying from that at amino acids 1092 to 1097 of SEQ ID NO:2 is SDSSPP (SEQ ID NO:20), LDSSPL (SEQ ID NO:21), LDSSPQ (SEQ ID NO:22), LDSLPP (SEQ ID NO:23), LDPSPP (SEQ ID NO:24), LDSPPP (SEQ ID NO:25), or VDSPPP (SEQ ID NO:26).

14. The modified Ty5 retrotransposon of claim 11 wherein said peptide portion specifically binds to a transcription factor.

15. The modified retrotransposon of claim 11 wherein said peptide portion specifically binds to a particular DNA sequence on said chromosome. location on a chromosome is accomplished.

16. A modified Ty5 retrotransposon comprising an integrase which directs integration of the modified Ty5 retrotransposon into a desired location on a chromosome, wherein said desired location is not silent chromatin, wherein a nucleotide sequence of said modified Ty5 retrotransposon does encode a peptide portion which binds specifically to a protein bound to the chromosome or to a particular DNA sequence on said chromosome.

* * * * *

UNITED STATES PATENT AND TRADEMARK OFFICE
CERTIFICATE OF CORRECTION

PATENT NO. : 6,228,647 B1
DATED : May 8, 2001
INVENTOR(S) : Voytas et al.

It is certified that error appears in the above-identified patent and that said Letters Patent is hereby corrected as shown below:

Column 3,
Line 1, replace "2940" with -- 29-40 --.

Column 5,
Line 59, replace "MRNA" with --mRNA --.

Column 6,
Line 46, replace "MRNA" with --mRNA --.

Column 10,
Line 1, replace "reining" with -- retaining --.

Column 16,
Line 34, replace "Sa/I" with -- SalI
Line, 35, replace "xbal" with --XbaI --.

Column 23 and 24,
Table 4, replace amino acid residue, 106, "Cya" with -- Cys --.

Column 66, claim 15,
Lines 33-34, delete "location on a chromosome is accomplished."

Signed and Sealed this

Eighth Day of January, 2002

Attest:

*Attesting Officer*

JAMES E. ROGAN
*Director of the United States Patent and Trademark Office*